United States Patent [19]
Goldberg

[11] Patent Number: 5,877,279
[45] Date of Patent: *Mar. 2, 1999

[54] MATERIALS FOR THE PRODUCTION OF NANOMETER STRUCTURES AND USE THEREOF

[75] Inventor: Edward B. Goldberg, Newton, Mass.

[73] Assignee: NanoFrames, LLC, Brookline, Mass.

[*] Notice: The term of this patent shall not extend beyond the expiration date of Pat. No. 5,864,013.

[21] Appl. No.: 322,760

[22] Filed: Oct. 13, 1994

[51] Int. Cl.⁶ .............................. C07K 14/00; C12P 21/06
[52] U.S. Cl. .......................... 530/350; 530/300; 530/324; 435/69.1; 435/69.7
[58] Field of Search .................................. 530/350, 300, 530/324; 435/69.1, 69.7

[56] References Cited

U.S. PATENT DOCUMENTS 3,532,593  10/1970  Young.

OTHER PUBLICATIONS

T.E. Creighton (ed.), 1984, *Proteins, Structures and Molecular Principles,* W.H. Freeman & Co, NY, pp. 25–28.

S.P. Parker (ed.), 1994, *Concise Encyclopedia of Science & Technology,* McGraw–Hill Inc, NY, p. 1354.

*Primary Examiner*—Karen Cochrane Carlson
*Attorney, Agent, or Firm*—Pennie & Edmonds LLP

[57] ABSTRACT

The present invention pertains to nanostructures. i.e. nanometer sized structures useful in the construction of microscopic and macroscopic structures. In particular, the present invention pertains to nanostructures based on bacteriophage T4 tail fiber proteins and variants thereof. More specifically, the present invention relates to polypeptides comprising modified gp37 tail fiber proteins of bacteriophage T4.

17 Claims, 25 Drawing Sheets

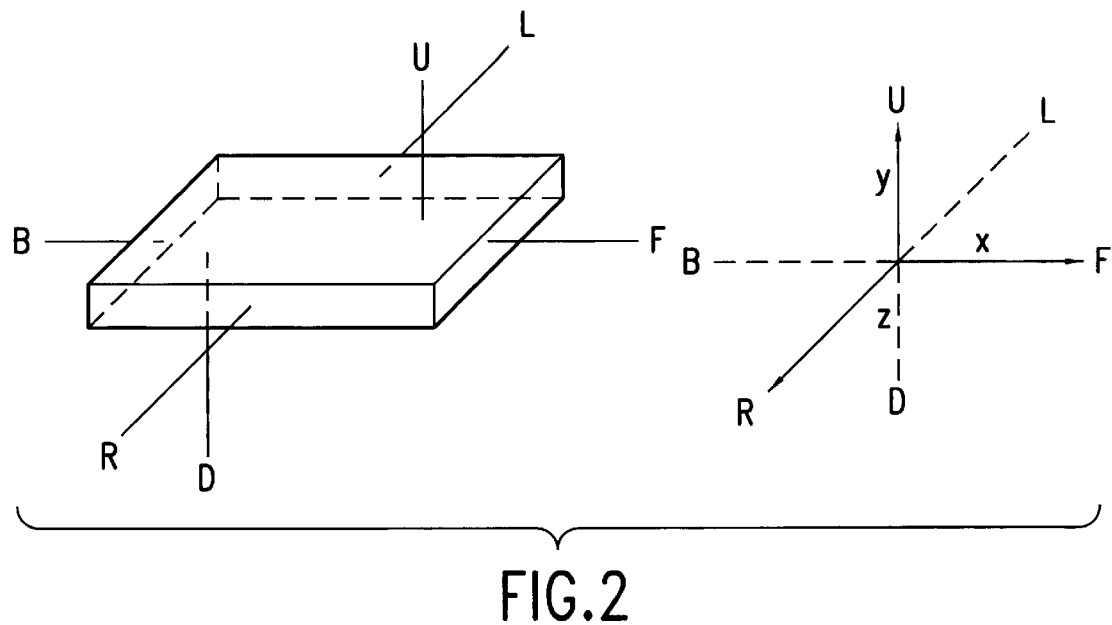
FIG.2
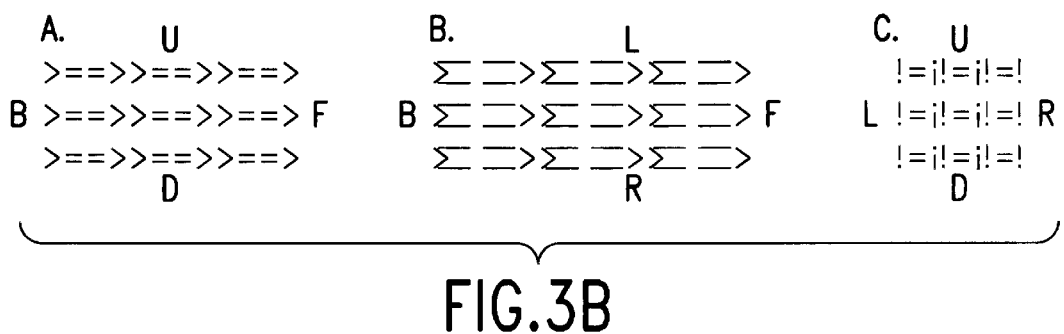
FIG.3A
FIG.3B

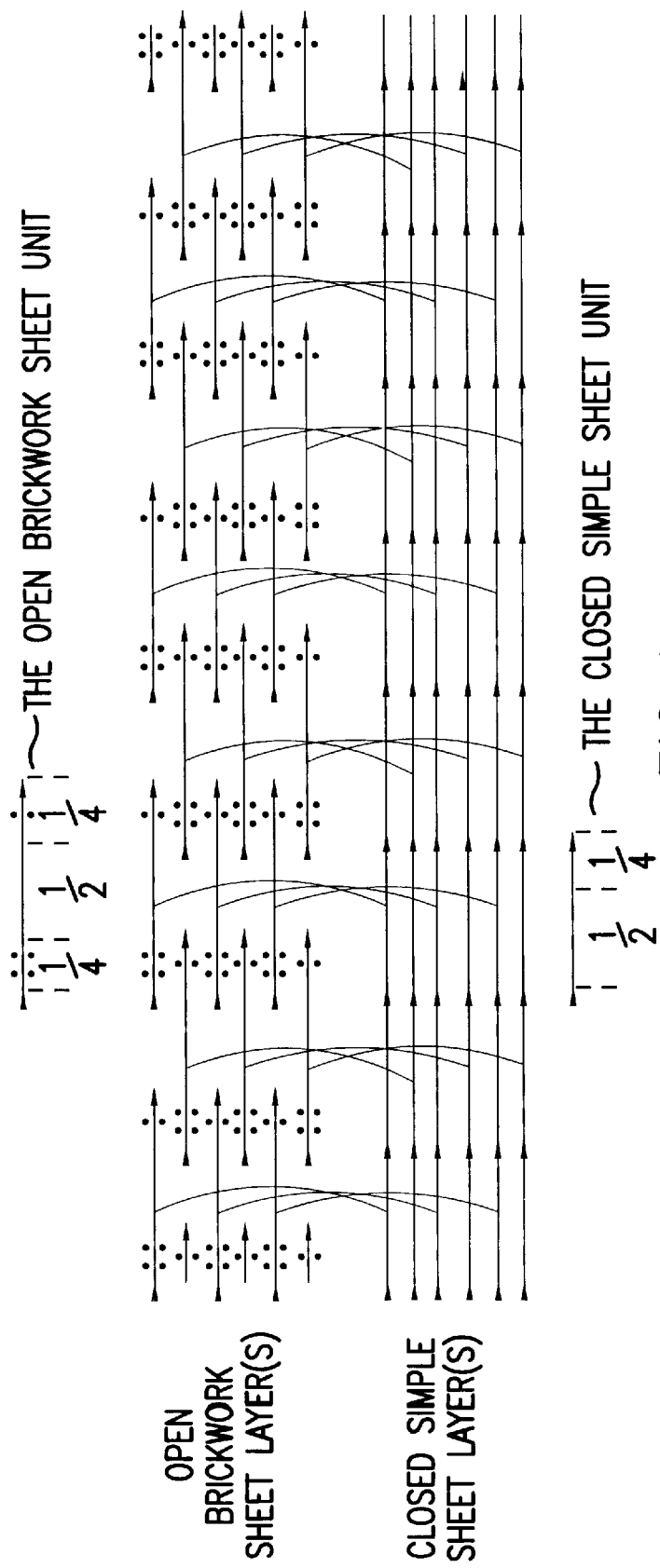
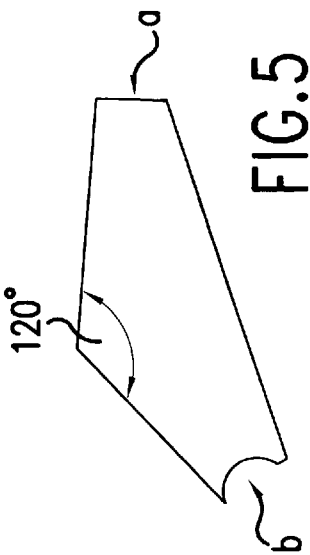
FIG. 4
FIG. 5

```
           |  10       |  20       |  30       |  40       |  50       |  60
    1   TAGGAGCCCG GGAGAATGGC CGAGATTAAA AGAGAATTCA GAGCAGAAGA TGGTCTGGAC    60
   61   GCAGGTGGTG ATAAAATAAT CAACGTAGCT TTAGCTGATC GTACCGTAGG AACTGACGGT   120
  121   GTTAACGTTG ATTACTTAAT TCAAGAAAAC ACAGTTCAAC AGTATGATCC AACTCGTGGA   180
  181   TATTTAAAAG ATTTTGTAAT CATTTATGAT AACCGCTTTT GGGCTGCTAT AAATGATATT   240
  241   CCAAAACCAG CAGGAGCTTT TAATAGCGGA CGCTGGAGAG CATTACGTAC CGATGCTAAC   300
  301   TGGATTACGG TTTCATCTGG TTCATATCAA TTAAAATCTG GTGAAGCAAT TCCGGTTAAC   360
  361   ACCGCAGCTG GAAATGACAT CACGTTTACT TTACCATCTT CTCCAATTGA TGGTGATACT   420
  421   ATCGTTCTCC AAGATATTGG AGGAAAACCT GGAGTTAACC AAGTTTTAAT TGTAGCTCCA   480
  481   GTACAAAGTA TTGTAAACTT TAGAGGTGAA CAGGTACGTT CAGTACTAAT GACTCATCCA   540
  541   AAGTCACAGC TAGTTTTAAT TTTTAGTAAT CGTCTGTGGC AAATGTATGT TGCTGATTAT   600
  601   AGTAGAGAAG CTATAGTTGT AACACCAGCG AATACTTATC AAGCGCAATC CAACGATTTT   660
  661   ATCGTACGTA GATTTACTTC TGCTGCACCA ATTAATGTCA AACTTCCAAG ATTTGCTAAT   720
  721   CATGGCGATA TTATTAATTT CGTCGATTTA GATAAACTAA ATCCGCTTTA TCATACAATT   780
  781   GTTACTACAT ACGATGAAAC GACTTCAGTA CAAGAAGTTG GAACTCATTC CATTGAAGGC   840
  841   CGTACATCGA TTGACGGTTT CTTGATGTTT GATGATAATG AGAAATTATG GAGACTGTTT   900
  901   GACGGGGATA GTAAAGCGCG TTTACGTATC ATAACGACTA ATTCAAACAT TCGTCCAAAT   960
  961   GAAGAAGTTA TGGTATTTGG TGCGAATAAC GGAACAACTC AAACAATTGA GCTTAAGCTT  1020
 1021   CCAACTAATA TTTCTGTTGG TGATACTGTT AAAATTTCCA TGAATTACAT GAGAAAAGGA  1080
 1081   CAAACAGTTA AAATCAAAGC TGCTGATGAA GATAAAATTG CTTCTTCAGT TCAATTGCTG  1140
 1141   CAATTCCCAA AACGCTCAGA ATATCCACCT GAAGCTGAAT GGGTTACAGT TCAAGAATTA  1200
 1201   GTTTTTAACG ATGAAACTAA TTATGTTCCA GTTTTGGAGC TTGCTTACAT AGAAGATTCT  1260
 1261   GATGGAAAAT ATTGGGTTGT ACAGCAAAAC GTTCCAACTG TAGAAAGAGT AGATTCTTTA  1320
 1321   AATGATTCTA CTAGAGCAAG ATTAGGCGTA ATTGCTTTAG CTACACAAGC TCAAGCTAAT  1380
 1381   GTCGATTTAG AAAATTCTCC ACAAAAAGAA TTAGCAATTA CTCCAGAAAC GTTAGCTAAT  1440
 1441   CGTACTGCTA CAGAAACTCG CAGAGGTATT GCAAGAATAG CAACTACTGC TCAAGTGAAT  1500
 1501   CAGAACACCA CATTCTCTTT TGCTGATGAT ATTATCATCA CTCCTAAAAA GCTGAATGAA  1560
 1561   AGAACTGCTA CAGAAACTCG TAGAGGTGTC GCAGAAATTG CTACGCAGCA AGAAACTAAT  1620
 1621   GCAGGAACCG ATGATACTAC AATCATCACT CCTAAAAAGC TTCAAGCTCG TCAAGGTTCT  1680
 1681   GAATCATTAT CTGGTATTGT AACCTTTGTA TCTACTGCAG GTGCTACTCC AGCTTCTAGC  1740
 1741   CGTGAATTAA ATGGTACGAA TGTTTATAAT AAAAACACTG ATAATTTAGT TGTTTCACCT  1800
 1801   AAAGCTTTGG ATCAGTATAA AGCTACTCCA ACACAGCAAG GTCCAGTAAT TTTAGCAGTT  1860
 1861   GAAAGTGAAG TAATTGCTGG ACAAAGTCAG CAAGGATGGG CAAATGCTGT TGTAACGCCA  1920
 1921   GAAACGTTAC ATAAAAAGAC ATCAACTGAT GGAAGAATTG GTTAATTGA AATTGCTACG  1980
 1981   CAAAGTGAAG TTAATACAGG AACTGATTAT ACTCGTGCAG TCACTCCTAA AACTTTAAAT  2040
 2041   GACCGTAGAG CAACTGAAAG TTTAAGTGGT ATAGCTGAAA TTGCTACACA AGTTGAATTC  2100
 2101   GACGCAGGCC TCGACGATAC TCGTATCTCT ACACCATTAA AAATTAAAAC CAGATTTAAT  2160
 2161   AGTACTGATC GTACTTCTGT TGTTGCTCTA TCTGGATTAG TTGAATCAGG AACTCTCTGG  2220
 2221   GACCATTATA CACTTAATAT TCTTGAAGCA AATGAGACAC AACGTGGTAC ACTTCGTGTA  2280
 2281   GCTACGCAGG TCGAAGCTGC TGCGGGAACA TTAGATAATG TTTTAATAAC TCCTAAAAAG  2340
```

FIG.6A

```
2341  CTTTTAGGTA CTAAATCTAC TGAAGCGCAA GAGGGTGTTA TTAAAGTTGC AACTCAGTCT  2400
2401  GAAACTGTGA CTGGAACGTC AGCAAATACT GCTGTATCTC CAAAAAATTT AAAATGGATT  2460
2461  GCGCAGAGTG AACCTACTTG GGCAGCTACT ACTGCAATAA GAGGTTTTGT TAAAACTTCA  2520
2521  TCTGGTTCAA TTACATTCGT TGGTAATGAT ACAGTCGGTT CTACCCAAGA TTTAGAACTG  2580
2581  TATGAGAAAA ATAGCTATGC GGTATCACCA TATGAATTAA ACCGTGTATT AGCAAATTAT  2640
2641  TTGCCACTAA AAGCAAAAGC TGCTGATACA AATTTATTGG ATGGTCTAGA TTCATCTCAG  2700
2701  TTCATTCGTA GGGATATTGC ACAGACGGTT AATGGTTCAC TAACCTTAAC CCAACAAACG  2760
2761  AATCTGAGTG CCCCTCTTGT ATCATCTAGT ACTGGTGAAT TGGTGGTTC ATTGGCCGCT  2820
2821  AATAGAACAT TTACCATCCC TAATACAGGA GCCCCGACTA GTATCGTTTT CGAAAAAGCT  2880
2881  CCTGCATCCG GGGCAAATCC TGCACAGTCA ATGAGTATTC GTCTATGGGG TAACCAATTT  2940
2941  GGCGGCGGTA GTGATACGAC CCGTTCGACA GTGTTTGAAG TTGGCGATGA CACATCTCAT  3000
3001  CACTTTTATT CTCAACGTAA TAAAGACGGT AATATAGCGT TAACATTAA TGGTACTGTA  3060
3061  ATGCCAATAA ACATTAATGC TTCCGGTTTG ATGAATGTGA ATGGCACTGC AACATTCGGT  3120
3121  CGTTCAGTTA CAGCCAATGG TGAATTCATC AGCAAGTCTG CAAATGCTTT TAGAGCAATA  3180
3181  AACGGTGATT ACGGATTCTT TATTCGTAAT GATGCCTCTA ATACCTATTT TTTGCTCACT  3240
3241  GCAGCCGGTG ATCAGACTGG TGGTTTTAAT GGATTACGCC CATTATTAAT TAATAATCAA  3300
3301  TCCGGTCAGA TTACAATTGG TGAAGGCTTA ATCATTGCCA AAGGTGTTAC TATAAATTCA  3360
3361  GGCGGTTTAA CTGTTAACTC GAGAATTCGT TCTCAGGGTA CTAAAACATC TGATTTATAT  3420
3421  ACCCGTGCGC AACATCTGA TACTGTAGGA TTCTGGTCAA TCGATATTAA TGATTCAGCC  3480
3481  ACTTATAACC AGTTCCCGGG TTATTTTAAA ATGGTTGAAA AAACTAATGA AGTGACTGGG  3540
3541  CTTCCATACT TAGAACGTGG CGAAGAAGTT AAATCTCCTG GTACACTGAC TCAGTTTGGT  3600
3601  AACACACTTG ATTCGCTTTA CCAAGATTCG ATTACTTATC CAACGACGCC AGAAGCGCGT  3660
3661  ACCACTCGCT GGACACGTAC ATGGCAGAAA ACCAAAAACT CTTGGTCAAG TTTTGTTCAG  3720
3721  GTATTTGACG GAGGTAACCC TCCTCAACCA TCTGATATCG GTGCTTTACC ATCTGATAAT  3780
3781  GCTACAATGG GGAATCTTAC TATTCGTGAT TTCTTGCGAA TTGGTAATGT TCGCATTGTT  3840
3841  CCTGACCCAG TGAATAAAAC GGTTAAATTT GAATGGGTTG AATAAGAGGT ATTATGGAAA  3900
3901  AATTTATGCC CGAGATTTGG ACAAGGATAT GTCCAAACGC CATTTTATCG GAAAGTAATT  3960
3961  CAGTAAGATA TAAAATAAGT ATAGCGGGTT CTTGCCCGCT TTCTACAGCA GGACCATCAT  4020
4021  ATGTTAAATT TCAGGATAAT CCTGTAGGAA GTCAAACATT TAGGCGCAGG CCTTCATTTA  4080
4081  AGAGTTTTTG ACCCTTCCAC CGGAGCATTA GTTGATAGTA AGTCATATGC TTTTTCGACT  4140
4141  TCAAATGATA CTACATCAGC TGCTTTTGTT AGTTTTCATG AATTCTTTGA CGAATAATCG  4200
4201  AATTGTTGCT ATATTAACTA GTGGAAAGGT TAATTTTCCT CCTGAAGTAG TATCTTGGTT  4260
4261  AACAACCGCC GGAACGTCTG CCTTTCCATC TGATTCTATA TTGTCAAGAT TTGACGTATC  4320
4321  ATATGCTGCT TTTTATACTT CTTCTAAAAG AGCTATCGCA TTAGAGCATG TTAAACTGAG  4380
4381  TAATAGAAAA AGCACAGATG ATTATCAAAC TATTTTAGAT GTTGTATTTG ACAGTTTAGA  4440
4441  AGATGTAGGA GCTACCGGGT TTCCAAGAAG AACGTATGAA AGTGTTGAGC AATTCATGTC  4500
4501  GGCAGTTGGT GGAACTAATA ACGAAATTGC GAGATTGCCA ACTTCAGCTG CTATAAGTAA  4560
4561  ATTATCTGAT TATAATTTAA TTCCTGGAGA TGTTCTTTAT CTTAAAGCTC AGTTATATGC  4620
4621  TGATGCTGAT TTACTTGCTC TTGGAACTAC AAATATATCT ATCCGTTTTT ATAATGCATC  4680
4681  TAACGGATAT ATTTCTTCAA CACAAGCTGA ATTTACTGGG CAAGCTGGGT CATGGGAATT  4740
```

FIG.6B

```
4741  AAAGGAAGAT TATGTAGTTG TTCCAGAAAA CGCAGTAGGA TTTACGATAT ACGCACAGAG  4800
4801  AACTGCACAA GCTGGCCAAG GTGGCATGAG AAATTTAAGC TTTTCTGAAG TATCAAGAAA  4860
4861  TGGCGGCATT TCGAAACCTG CTGAATTTGG CGTCAATGGT ATTCGTGTTA ATTATATCTG  4920
4921  CGAATCCGCT TCACCTCCGG ATATAATGGT ACTTCCTACG CAAGCATCGT CTAAAACTGG  4980
4981  TAAAGTGTTT GGGCAAGAAT TTAGAGAAGT TTAAATTGAG GGACCCTTCG GGTTCCCTTT  5040
5041  TTCTTTATAA ATACTATTCA AATAAAGGGG CATACAATGG CTGATTTAAA AGTAGGTTCA  5100
5101  ACAACTGGAG GCTCTGTCAT TTGGCATCAA GGAAATTTTC CATTGAATCC AGCCGGTGAC  5160
5161  GATGTACTCT ATAAATCATT TAAAATATAT TCAGAATATA ACAAACCACA AGCTGCTGAT  5220
5221  AACGATTTCG TTTCTAAAGC TAATGGTGGT ACTTATGCAT CAAAGGTAAC ATTTAACGCT  5280
5281  GGCATTCAAG TCCCATATGC TCCAAACATC ATGAGCCCAT GCGGGATTTA TGGGGGTAAC  5340
5341  GGTGATGGTG CTACTTTTGA TAAAGCAAAT ATCGATATTG TTTCATGGTA TGCCGTAGGA  5400
5401  TTTAAATCGT CATTTGGTTC AACAGGCCGA ACTGTTGTAA TTAATACACG CAATGGTGAT  5460
5461  ATTAACACAA AAGGTGTTGT GTCGGCAGCT GGTCAAGTAA GAAGTGGTGC GGCTGCTCCT  5520
5521  ATAGCAGCGA ATGACCTTAC TAGAAAGGAC TATGTTGATG GAGCAATAAA TACTGTTACT  5580
5581  GCAAATGCAA ACTCTAGGGT GCTACGGTCT GGTGACACCA TGACAGGTAA TTTAACAGCG  5640
5641  CCAAACTTTT TCTCGCAGAA TCCTGCATCT CAACCCTCAC ACGTTCCACG ATTTGACCAA  5700
5701  ATCGTAATTA AGGATTCTGT TCAAGATTTC GGCTATTATT AAGAGGACTT ATGGCTACTT  5760
5761  TAAAACAAAT ACAATTTAAA AGAAGCAAAA TCGCAGGAAC ACGTCCTGCT GCTTCAGTAT  5820
5821  TAGCCGAAGG TGAATTGGCT ATAAACTTAA AAGATAGAAC AATTTTTACT AAAGATGATT  5880
5881  CAGGAAATAT CATCGATCTA GGTTTTGCTA AAGGCGGGCA AGTTGATGGC AACGTTACTA  5940
5941  TTAACGGACT TTTGAGATTA AATGGCGATT ATGTACAAAC AGGTGGAATG ACTGTAAACG  6000
6001  GACCCATTGG TTCTACTGAT GGCGTCACTG GAAAAATTTT CAGATCTACA CAGGGTTCAT  6060
6061  TTTATGCAAG AGCAACAAAC GATACTTCAA ATGCCCATTT ATGGTTTGAA AATGCCGATG  6120
6121  GCACTGAACG TGGCGTTATA TATGCTCGCC CTCAAACTAC AACTGACGGT GAAATACGCC  6180
6181  TTAGGGTTAG ACAAGGAACA GGAAGCACTG CCAACAGTGA ATTCTATTTC CGCTCTATAA  6240
6241  ATGGAGGCGA ATTCAGGCT AACCGTATTT TAGCATCAGA TTCGTTAGTA ACAAAACGCA  6300
6301  TTGCGGTTGA TACCGTTATT CATGATGCCA AAGCATTTGG ACAATATGAT TCTCACTCTT  6360
6361  TGGTTAATTA TGTTTATCCT GGAACCGGTG AAACAAATGG TGTAAACTAT CTTCGTAAAG  6420
6421  TTCGCGCTAA GTCCGGTGGT ACAATTTATC ATGAAATTGT TACTGCACAA ACAGGCCTGG  6480
6481  CTGATGAAGT TTCTTGGTGG TCTGGTGATA CACCAGTATT TAAACTATAC GGTATTCGTG  6540
6541  ACGATGGCAG AATGATTATC CGTAATAGCC TTGCATTAGG TACATTCACT ACAAATTTCC  6600
6601  CGTCTAGTGA TTATGGCAAC GTCGGTGTAA TGGGCGATAA GTATCTTGTT CTCGGCGACA  6660
6661  CTGTAACTGG CTTGTCATAC AAAAAAACTG GTGTATTTGA TCTAGTTGGC GGTGGATATT  6720
6721  CTGTTGCTTC TATTACTCCT GACAGTTTCC GTAGTACTCG TAAAGGTATA TTTGGTCGTT  6780
6781  CTGAGGACCA AGGCGCAACT TGGATAATGC CTGGTACAAA TGCTGCTCTC TTGTCTGTTC  6840
6841  AAACACAAGC TGATAATAAC AATGCTGGAG ACGGACAAAC CCATATCGGG TACAATGCTG  6900
6901  GCGGTAAAAT GAACCACTAT TTCCGTGGTA CAGGTCAGAT GAATATCAAT ACCCAACAAG  6960
6961  GTATGGAAAT TAACCCGGGT ATTTTGAAAT TGGTAACTGG CTCTAATAAT GTACAATTTT  7020
7021  ACGCTGACGG AACTATTTCT TCCATTCAAC CTATTAAATT AGATAACGAG ATATTTTTAA  7080
7081  CTAAATCTAA TAATACTGCG GGTCTTAAAT TTGGAGCTCC TAGCCAAGTT GATGGCACAA  7140
```

FIG.6C

```
7141  GGACTATCCA ATGGAACGGT GGTACTCGCG AAGGACAGAA TAAAAACTAT GTGATTATTA  7200
7201  AAGCATGGGG TAACTCATTT AATGCCACTG GTGATAGATC TCGCGAAACG GTTTTCCAAG  7260
7261  TATCAGATAG TCAAGGATAT TATTTTTATG CTCATCGTAA AGCTCCAACC GGCGACGAAA  7320
7321  CTATTGGACG TATTGAAGCT CAATTTGCTG GGGATGTTTA TGCTAAAGGT ATTATTGCCA  7380
7381  ACGGAAATTT TAGAGTTGTT GGGTCAAGCG CTTTAGCCGG CAATGTTACT ATGTCTAACG  7440
7441  GTTTGTTTGT CCAAGGTGGT TCTTCTATTA CTGGACAAGT TAAAATTGGC GGAACAGCAA  7500
7501  ACGCACTGAG AATTTGGAAC GCTGAATATG GTGCTATTTT CCGTCGTTCG GAAAGTAACT  7560
7561  TTTATATTAT TCCAACCAAT CAAAATGAAG GAGAAAGTGG AGACATTCAC AGCTCTTTGA  7620
7621  GACCTGTGAG AATAGGATTA AACGATGGCA TGGTTGGGTT AGGAAGAGAT TCTTTTATAG  7680
7681  TAGATCAAAA TAATGCTTTA ACTACGATAA ACAGTAACTC TCGCATTAAT GCCAACTTTA  7740
7741  GAATGCAATT GGGGCAGTCG GCATACATTG ATGCAGAATG TACTGATGCT GTTCGCCCGG  7800
7801  CGGGTGCAGG TTCATTTGCT TCCCAGAATA ATGAAGACGT CCGTGCGCCC TTCTATATGA  7860
7861  ATATTGATAG AACTGATGCT AGTGCATATG TTCCTATTTT GAAACAACGT TATGTTCAAG  7920
7921  GCAATGGCTG CTATTCATTA GGGACTTTAA TTAATAATGG TAATTTCCGA GTTCATTACC  7980
7981  ATGGCGGCGG AGATAACGGT TCTACAGGTC CACAGACTGC TGATTTTGGA TGGGAATTTA  8040
8041  TTAAAAACGG TGATTTTATT TCACCTCGCG ATTTAATAGC AGGCAAAGTC AGATTTGATA  8100
8101  GAACTGGTAA TATCACTGGT GGTTCTGGTA ATTTTGCTAA CTTAAACAGT ACAATTGAAT  8160
8161  CACTTAAAAC TGATATCATG TCGAGTTACC CAATTGGTGC TCCGATTCCT TGGCCGAGTG  8220
8221  ATTCAGTTCC TGCTGGATTT GCTTGATGG AAGGTCAGAC CTTTGATAAG TCCGCATATC  8280
8281  CAAAGTTAGC TGTTGCATAT CCTAGCGGTG TTATTCCAGA TATGCGCGGG CAAACTATCA  8340
8341  AGGGTAAACC AAGTGGTCGT GCTGTTTTGA GCGCTGAGGC AGATGGTGTT AAGGCTCATA  8400
8401  GCCATAGTGC ATCGGCTTCA AGTACTGACT TAGGTACTAA AACCACATCA AGCTTTGACT  8460
8461  ATGGTACGAA GGGAACTAAC AGTACGGGTG GACACACTCA CTCTGGTAGT GGTTCTACTA  8520
8521  GCACAAATGG TGAGCACAGC CACTACATCG AGGCATGGAA TGGTACTGGT GTAGGTGGTA  8580
8581  ATAAGATGTC ATCATATGCC ATATCATACA GGGCGGGTGG GAGTAACACT AATGCAGCAG  8640
8641  GGAACCACAG TCACACTTTC TCTTTTGGGA CTAGCAGTGC TGGCGACCAT TCCCACTCTG  8700
8701  TAGGTATTGG TGCTCATACC CACACGGTAG CAATTGGATC ACATGGTCAT ACTATCACTG  8760
8761  TAAATAGTAC AGGTAATACA GAAAACACGG TTAAAAACAT TGCTTTTAAC TATATCGTTC  8820
8821  GTTTAGCATA AGGAGAGGGG CTTCGGCCCT TCTAA                              8855
              |   10     |    20    |    30    |    40    |    50    |    60
```

FIG. 6D

```
  1      TAGGAGCCCCGGGAGA ATG GCC GAG ATT AAA AGA GAA TTC AGA GCA GAA GAT GGT CTG GAC GCA     63
  1                       M   A   E   I   K   R   E   F   R   A   E   D   G   L   D   A      16

64      GGT GGT GAT AAA ATA ATC AAC GTA GCT TTA GCT GAT CGT ACC GTA GGA ACT GAC GGT GTT    123
 17       G   G   D   K   I   I   N   V   A   L   A   D   R   T   V   G   T   D   G   V      36

124      AAC GTT GAT TAC TTA ATT CAA GAA AAC ACA GTT CAA CAG TAT GAT CCA ACT CGT GGA TAT    183
 37       N   V   D   Y   L   I   Q   E   N   T   V   Q   Q   Y   D   P   T   R   G   Y      56

184      TTA AAA GAT TTT GTA ATC ATT TAT GAT AAC CGC TTT TGG GCT GCT ATA AAT GAT ATT CCA    243
 57       L   K   D   F   V   I   I   Y   D   N   R   F   W   A   A   I   N   D   I   P      76

244      AAA CCA GCA GGA GCT TTT AAT AGC GGA CGC TGG AGA GCA TTA CGT GAA GCA ATT TCG GTT    303
 77       K   P   A   G   A   F   N   S   G   R   W   R   A   L   R   E   A   I   S   V      96

304      ATT ACG GTT TCA TCT GGT TCA TAT CAA TTA AAA TCT GGT GAA GCA ATT TCG GTT AAC ACC    363
 97       I   T   V   S   S   G   S   Y   Q   L   K   S   G   E   A   I   S   V   N   T     116

364      GCA GCT GGA AAT GAC ATC ACG TTT ACT TTA CCA TCT TCT CCA ATT GAT GGT GAT ACT ATC    423
117       A   A   G   N   D   I   T   F   T   L   P   S   S   P   I   D   G   D   T   I     136

424      GTT CTC CAA GAT ATT GGA GGA AAA CCT GGA GTT AAC CAA GTT TTA ATT GTA GCT CCA GTA    483
137       V   L   Q   D   I   G   G   K   P   G   V   N   Q   V   L   I   V   A   P   V     156

484      CAA AGT ATT GTA AAC TTT AGA GGT GAA CAG CGT TCA GTA CTA ATG ACT CAT CCA AAG        543
157       Q   S   I   V   N   F   R   G   E   Q   R   S   V   L   M   T   H   P   K         176
```

FIG.7A

| | | | | | | | | | | |
|---|---|---|---|---|---|---|---|---|---|---|
| 544 | TCA | CAG | CTA | GTT | TTA | ATT | TTT | AGT | AAT | CGT | CTG | TGG | CAA | ATG | TAT | GTT | GCT | GAT | TAT | AGT | 603 |
| 177 | S | Q | L | V | L | I | F | S | N | R | L | W | Q | M | Y | V | A | D | Y | S | 196 |

| 604 | AGA | GAA | GCT | ATA | GTT | GTA | ACA | CCA | GCG | AAT | ACT | TAT | CAA | GCG | CAA | TCC | CAA | AAC | GAT | TTT | ATC | 663 |
| 197 | R | E | A | I | V | V | T | P | A | N | T | Y | Q | A | Q | S | Q | N | D | F | I | 216 |

| 664 | GTA | CGT | AGA | TTT | ACT | TCT | GCT | GCA | CCA | ATT | AAT | GTC | AAA | CTT | CCA | AGA | TTT | GCT | AAT | CAT | 723 |
| 217 | V | R | R | F | T | S | A | A | P | I | N | V | K | L | P | R | F | A | N | H | 236 |

| 724 | GGC | GAT | ATT | ATT | AAT | TTC | GTC | GAT | TTA | GAT | AAA | CTA | AAT | CCG | CTT | TAT | CAT | ACA | ATT | GTT | 783 |
| 237 | G | D | I | I | N | F | V | D | L | D | K | L | N | P | L | Y | H | T | I | V | 256 |

| 784 | ACT | ACA | TAC | GAT | GAA | ACG | ACT | TCA | GTA | CAA | GAA | GTT | GGA | ACT | CAT | TCC | ATT | GAA | GGC | CGT | 843 |
| 257 | T | T | Y | D | E | T | T | S | V | Q | E | V | G | T | H | S | I | E | G | R | 276 |

| 844 | ACA | TCG | ATT | GAC | GGT | TTC | TTG | ATG | TTT | GAT | GAT | AAT | GAG | AAA | TTA | TGG | AGA | CTG | TTT | GAC | 903 |
| 277 | T | S | I | D | G | F | L | M | F | D | D | N | E | K | L | W | R | L | F | D | 296 |

| 904 | GGG | GAT | AGT | AAA | GCG | CGT | TTA | CGT | ATC | ATA | ACG | ACT | AAT | TCA | AAC | ATT | CGT | CCA | AAT | GAA | 963 |
| 297 | G | D | S | K | A | R | L | R | I | I | T | T | N | S | N | I | R | P | N | E | 316 |

| 964 | GAA | GTT | ATG | GTA | TTT | GGT | GCG | AAT | AAC | GGA | ACA | ACT | CAA | ACA | ATT | GAG | CTT | AAG | CTT | CCA | 1023 |
| 317 | E | V | M | V | F | G | A | N | N | G | T | T | Q | T | I | E | L | K | L | P | 336 |

| 1024 | ACT | AAT | ATT | TCT | GTT | GGT | GAT | ACT | GTT | AAA | ATT | TCC | ATG | AAT | TAC | ATG | AGA | AAA | GGA | CAA | 1083 |
| 337 | T | N | I | S | V | G | D | T | V | K | I | S | M | N | Y | M | R | K | G | Q | 356 |

FIG.7B

| | | | | | | | | | | | |
|---|---|---|---|---|---|---|---|---|---|---|---|
| 1084 | ACA | GTT | AAA | ATC | AAA | GCT | GCT | GAT | GAA | ATT | GCT | TCT | TCA | GTT | CAA | TTG | CTG | CAA | 1143 |
| 357 | T | V | K | I | K | A | A | D | E | I | A | S | S | V | Q | L | L | Q | 376 |
| 1144 | TTC | CCA | AAA | CGC | TCA | GAA | TAT | CCA | CCT | GAA | GCT | GAA | TGG | GTT | ACA | GAA | TTA | GTT | 1203 |
| 377 | F | P | K | R | S | E | Y | P | P | E | A | E | W | V | T | E | L | V | 396 |
| 1204 | TTT | AAC | GAT | GAA | ACT | AAT | TAT | GTT | CCA | GTT | TTG | GAG | CTT | GCT | TAC | ATA | GAA | GAT | TCT | GAT | 1263 |
| 397 | F | N | D | E | T | N | Y | V | P | V | L | E | L | A | Y | I | E | D | S | D | 416 |
| 1264 | GGA | AAA | TAT | TGG | GTT | GTA | CAG | CAA | AAC | GTT | CCA | ACT | GTA | GAA | AGA | GTA | GAT | TCT | TTA | AAT | 1323 |
| 417 | G | K | Y | W | V | V | Q | Q | N | V | P | T | V | E | R | V | D | S | L | N | 436 |
| 1324 | GAT | TCT | ACT | AGA | GCA | AGA | TTA | GGC | GTA | ATT | GCT | TTA | GCT | ACA | CAA | GCT | CAA | GCT | AAT | GTC | 1383 |
| 437 | D | S | T | R | A | R | L | G | V | I | A | L | A | T | Q | A | Q | A | N | V | 456 |
| 1384 | GAT | TTA | GAA | AAT | TCT | CCA | CAA | AAA | GAA | TTA | GCA | ATT | ACT | CCA | GAA | ACG | TTA | GCT | AAT | CGT | 1443 |
| 457 | D | L | E | N | S | P | Q | K | E | L | A | I | T | P | E | T | L | A | N | R | 476 |
| 1444 | ACT | GCT | ACA | GAA | ACT | ACA | TTC | TCT | TTT | GCT | GAT | GAT | ATT | ATC | ATC | ACT | CCT | AAA | AAG | CTG | AAT | CAC | 1503 |
| 477 | T | A | T | E | T | T | F | S | F | A | D | D | I | I | I | T | P | K | K | L | N | Q | 496 |
| 1504 | AAC | ACC | ACA | TTC | TCT | TTT | GCT | GAT | GAT | ATT | ATC | ATC | ACT | CCT | AAA | AAG | CTG | AAT | GAA | AGA | 1563 |
| 497 | N | T | T | F | S | F | A | D | D | I | I | I | T | P | K | K | L | N | E | R | 516 |
| 1564 | ACT | GCT | ACA | GAA | ACT | CGT | AGA | GGT | GTC | GCA | GAA | ATT | GCT | ACG | CAG | CAA | GAA | ACT | AAT | GCA | 1623 |
| 517 | T | A | T | E | T | R | R | G | V | A | E | I | A | T | Q | Q | E | T | N | A | 536 |

FIG. 7C

```
1624  GGA ACC GAT GAT ACT ACA ATC ATC ACT CCT AAA AAG CTT CAA GCT CGT CAA GGT TCT GAA  1683
 537   G   T   D   D   T   T   I   I   T   P   K   K   L   Q   A   R   Q   G   S   E    556

1684  TCA TTA TCT GGT ATT GTA ACC TTT GTA TCT ACT GCA GGT GCT ACT CCA GCT TCT AGC CGT  1743
 557   S   L   S   G   I   V   T   F   V   S   T   A   G   A   T   P   A   S   S   R    576

1744  GAA TTA AAT GGT ACC AAT GTT TAT AAT AAA AAC ACT GAT AAT TTA GTT GTT TCA CCT AAA  1803
 577   E   L   N   G   T   N   V   Y   N   K   N   T   D   N   L   V   V   S   P   K    596

1804  GCT TTG GAT CAG TAT AAA GCT ACT CCA ACA CAG CAA GGT GCA GTA ATT TTA GCA GTT GAA  1863
 597   A   L   D   Q   Y   K   A   T   P   T   Q   Q   G   A   V   I   L   A   V   E    616

1864  AGT GAA GTA ATT GCT GGA CAA AGT ACA ACT GAT CAG CAA GGA TGG GCA AAT GCT GTT GTA ACG CCA GAA  1923
 617   S   E   V   I   A   G   Q   S   T   T   D   Q   Q   G   W   A   N   A   V   V   T   P   E    636

1924  ACG TTA CAT AAA AAG ACA ATA GGA ACT GAT TAT ACT CGT GCA GTC ACT CCT AAA ACT TTA ATT GCT ACG CAA  1983
 637   T   L   H   K   K   T   I   G   L   I   E   I   A   T   Q    656

1984  AGT GAA GTT AAT ACA GGA AAT ACT GGT GAT TAT ACT CGT GCA GTC ACT CCT AAA ACT TTA AAT GAC  2043
 657   S   E   V   N   T   G   D   Y   T   R   A   V   T   P   K   T   L   N   D    676

2044  CGT AGA GCA ACT GAA AGT TTA AGT GGT ATA GCT GAA ATT GCT ACA CAA GTT GAA TTC GAC  2103
 677   R   R   A   T   E   S   L   S   G   I   A   E   I   A   T   Q   V   E   F   D    696

2104  GCA GGC GTC GAC GAT ACT CGT ATC TCT ACA CCA TTA AAA ATT AAA ACC AGA TTT AAT AGT  2163
 697   A   G   V   D   D   T   R   I   S   T   P   L   K   I   K   T   R   F   N   S    716
```

FIG.7D

```
2164  ACT GAT CGT ACT TCT GTT GCT CTA TCT GGA TTA GTT GAA TCA GGA ACT CTC TGG GAC  2223
717    T   D   R   T   S   V   A   L   S   G   L   V   E   S   G   T   L   W   D   736

2224  CAT TAT ACA CTT AAT ATT CTT GAA GCA AAT GAG ACA CAA CCT GGT ACA CTT CCT GTA GCT  2283
737    H   Y   T   L   N   I   L   E   A   N   E   T   Q   R   G   T   L   R   V   A   756

2284  ACG CAG GTC GAA GCT GCT GCC GGA ACA TTA GAT AAT GTT TTA ATA ACT CCT AAA AAG CTT  2343
757    T   Q   V   E   A   A   A   G   T   L   D   N   V   L   I   T   P   K   K   L   776

2344  TTA GGT ACT AAA TCT GAA GCC CAA GAG CGT GTT ATT AAA GTT GCA ACT CAG TCT GAA  2403
777    L   G   T   K   S   E   A   Q   E   G   V   I   K   V   A   T   Q   S   E   796

2404  ACT GTG ACT GGA ACG TCA GCA AAT ACT GCT GTA TCT CCA AAA AAT TTA AAA TGG ATT GCG  2463
797    T   V   T   G   T   S   A   N   T   A   V   S   P   K   N   L   K   W   I   A   816

2464  CAG AGT GAA CCT ACT TGG GCA GCT ACT ACT GCA ATA AGA GGT TTT GTT AAA ACT TCA TCT  2523
817    Q   S   E   P   T   W   A   A   T   T   A   I   R   G   F   V   K   T   S   S   836

2524  GGT TCA ATT ACA TTC GTT GGT AAT GAT ACA GTC GGT TCT ACC CAA GAT TTA GAA CTG TAT  2583
837    G   S   I   T   F   V   G   N   D   T   V   G   S   T   Q   D   L   E   L   Y   856

2584  GAG AAA AAT AGC TAT GCC GTA TCA CCA TAT GAA TTA AAC CGT GTA TTA GCA AAT TAT TTG  2643
857    E   K   N   S   Y   A   V   S   P   Y   E   L   N   R   V   L   A   N   Y   L   876

2644  CCA CTA AAA GCA AAA GCT GCT GAT ACA AAT TTA GAT GGT CTA GAT TCA TCT CAG TTC  2703
877    P   L   K   A   K   A   A   D   T   N   L   D   G   L   D   S   S   Q   F   896
```

FIG.7E

| | | | | | | | | | | | | | | | | | | | | |
|---|---|---|---|---|---|---|---|---|---|---|---|---|---|---|---|---|---|---|---|---|
|2704|ATT|CGT|AGG|GAT|ATT|GCA|CAG|ACG|GTT|AAT|GGT|TCA|CTA|ACC|CAA|CAA|ACG|AAT|2763|
|897|I|R|R|D|I|A|Q|T|V|N|G|S|L|T|Q|Q|T|N|916|
|2764|CTG|AGT|GCC|CCT|CTT|GTA|TCA|TCT|AGT|ACT|GGT|GAA|TTT|GGT|GGT|TCA|TTG|GCC|GCT|AAT|2823|
|917|L|S|A|P|L|V|S|S|S|T|G|E|F|G|G|S|L|A|A|N|936|
|2824|AGA|ACA|TTT|ACC|ATC|CGT|AAT|ACA|GGA|GCC|CCG|ACT|AGT|ATC|GTT|TTC|GAA|AAA|GGT|CCT|2883|
|937|R|T|F|T|I|R|N|T|G|A|P|T|S|I|V|F|E|K|G|P|956|
|2884|GCA|TCC|GGG|GCA|AAT|CCT|GCA|CAG|TCA|ATG|AGT|ATT|CGT|GTA|TGG|GGT|AAC|CAA|TTT|GCC|2943|
|957|A|S|G|A|N|P|A|Q|S|M|S|I|R|V|W|G|N|Q|F|G|976|
|2944|GGC|GGT|AGT|GAT|ACG|ACC|CGT|TCG|ACA|GTG|TTT|GAA|GTT|GGC|GAT|GAC|ACA|TCT|CAT|CAC|3003|
|977|G|G|S|D|T|T|R|S|T|V|F|E|V|G|D|D|T|S|H|H|996|
|3004|TTT|TAT|TCT|CAA|CGT|AAT|AAA|GAC|GGT|AAT|ATA|GCC|TTT|AAC|ATT|AAT|GGT|ACT|GTA|ATG|3063|
|997|F|Y|S|Q|R|N|K|D|G|N|I|A|F|N|I|N|G|T|V|M|1016|
|3064|CCA|ATA|AAC|ATT|AAT|GCT|TCC|GGT|TTG|ATG|AAT|GTG|AAT|GGC|ACT|GCA|ACA|TTC|GGT|CGT|3123|
|1017|P|I|N|I|N|A|S|G|L|M|N|V|N|G|T|A|T|F|G|R|1036|
|3124|TCA|GTT|ACA|GCC|AAT|GGT|GAA|TTC|ATC|AGC|AAG|TCT|GCA|AAT|GCT|TTT|AGA|GCA|ATA|AAC|3183|
|1037|S|V|T|A|N|G|E|F|I|S|K|S|A|N|A|F|R|A|I|N|1056|
|3184|GGT|GAT|TAC|GGA|TTC|TTT|ATT|CGT|AAT|GAT|GCC|TCT|AAT|ACC|TAT|TTT|TTG|CTC|ACT|GCA|3243|
|1057|G|D|Y|G|F|F|I|R|N|D|A|S|N|T|Y|F|L|L|T|A|1076|

FIG. 7F

```
3244 GCC GGT GAT CAG ACT GGT GGT TTT AAT GGA TTA CGC CCA TTA ATT AAT AAT CAA TCC 3303
1077  A   G   D   Q   T   G   G   F   N   G   L   R   P   L   L   I   N   N   Q   S  1096

3304 GGT CAG ATT ACA ATT GGT GAA GGC TTA ATC ATT GCC AAA GGT GTT ACT ATA AAT TCA GGC 3363
1097  G   Q   I   T   I   G   E   G   L   I   I   A   K   G   V   T   I   N   S   G  1116

3364 GGT TTA ACT GTT AAC TCG AGA ATT CGT TCT CAG GGT ACT AAA ACA TCT GAT TTA TAT ACC 3423
1117  G   L   T   V   N   S   R   I   R   S   Q   G   T   K   T   S   D   L   Y   T  1136

3424 CGT GCG CCA ACA TCT GAT ACT GTA GGA TTC TGG TCA ATC GAT ATT AAT GAT TCA GCC ACT 3483
1137  R   A   P   T   S   D   T   V   G   F   W   S   I   D   I   N   D   S   A   T  1156

3484 TAT AAC CAG TTC CCC GGT TAT TTT AAA ATG GTT GAA AAA ACT AAT GAA GTG ACT GGG CTT 3543
1157  Y   N   Q   F   P   G   Y   F   K   M   V   E   K   T   N   E   V   T   G   L  1176

3544 CCA TAC TTA GAA CGT GGC GAA GAA GTT AAA TCT CCT GGT ACA CTG ACT CAG TTT GGT AAC 3603
1177  P   Y   L   E   R   G   E   E   V   K   S   P   G   T   L   T   Q   F   G   N  1196

3604 ACA CTT GAT TCG CTT TAC CAA GAT TGG ATT ACT TAT CCA ACG ACG CCA GAA GCG CGT ACC 3663
1197  T   L   D   S   L   Y   Q   D   W   I   T   Y   P   T   T   P   E   A   R   T  1216

3664 ACT CGC TGG ACA CGT ACA TGG CAG AAA ACC AAA AAC TCT TGG TCA AGT TTT GTT CAG GTA 3723
1217  T   R   W   T   R   T   W   Q   K   T   K   N   S   W   S   S   F   V   Q   V  1236

3724 TTT GAC GGA AAC CCT CCT CAA CCA CCA TCT GAT ATC GGT GCT TTA CCA TCT GAT AAT GCT 3783
1237  F   D   G   N   P   P   Q   P   P   S   D   I   G   A   L   P   S   D   N   A  1256
```

FIG.7G

```
3784  ACA ATG GGG AAT CTT ACT ATT CGT GAT TTC TTG CGA ATT GGT AAT GTT CGC ATT GTT CCT  3843
1257    T   M   G   N   L   T   I   R   D   F   L   R   I   G   N   V   R   I   V   P  1276

3844  GAC CCA GTG AAT AAA ACG GTT AAA TTT GAA TGG GTT GAA TAA GAGGTATT ATG GAA AAA TTT  3905
1277    D   P   V   N   K   T   V   K   F   E   W   V   E   *             M   E   K   F     4

3906  ATG GCC GAG ATT TGG ACA AGG ATA TGT CCA AAC GCC ATT TTA TCG GAA AGT AAT TCA GTA  3965
   5    M   A   E   I   W   T   R   I   C   P   N   A   I   L   S   E   S   N   S   V    24

3966  AGA TAT AAA ATA AGT ATA GCC GGT TCT TGC CCG CTT TCT ACA GCA GGA CCA TCA TAT GTT  4025
  25    R   Y   K   I   S   I   A   G   S   C   P   L   S   T   A   G   P   S   Y   V    44

4026  AAA TTT CAG GAT AAT CCT GTA GGA AGT CAA ACA TTT AGG CGC AGG CCT TCA TTT AAG AGT  4085
  45    K   F   Q   D   N   P   V   G   S   Q   T   F   R   R   R   P   S   F   K   S    64

4086  TTT TGA CCCTTCCACCGGAGCATTAGTTGATAGTAAGTCAT ATG CTT TTT CGA CTT CAA ATG ATA CTA  4153
  65    F   *                                      M   L   F   R   L   Q   M   I   L     9

4154  CAT CAG CTG CTT TTG TTA GTT TTC ATG AAT TCT TTG ACG AAT AAT CGA ATT GTT GCT ATA  4213
  10    H   Q   L   L   L   L   V   F   M   N   S   L   T   N   N   R   I   V   A   I    29

4214  TTA ACT AGT GGA AAG GTT AAT TTT CCT CCT GAA GTA GTA TCT TGG TTA AGA ACC GCC GGA  4273
  30    L   T   S   G   K   V   N   F   P   P   E   V   V   S   W   L   R   T   A   G    49

4274  ACG TCT GCC TTT CCA TCT GAT TCT ATA TTG TCA AGA TTT GAC GTA TCA TAT GCT GCT TTT  4333
  50    T   S   A   F   P   S   D   S   I   L   S   R   F   D   V   S   Y   A   A   F    69
```

FIG. 7H

```
4334 TAT ACT TCT TCT AAA AGA GCT ATC GCA TTA GAC CAT GTT AAA CTG AGT AAT AGA AAA AGC 4393
  70  Y   T   S   S   K   R   A   I   A   L   E   H   V   K   L   S   N   R   K   S   89

4394 ACA GAT GAT TAT CAA ACT ATT TTA GAT GTT GTA TTT GAC AGT TTA GAA GAT GTA GGA GCT 4453
  90  T   D   D   Y   Q   T   I   L   D   V   V   F   D   S   L   E   D   V   G   A  109

4454 ACC GGG TTT CCA AGA AGA ACG TAT GAA AGT GTT GAC CAA TTC ATG TCG GCA GTT GGT GGA 4513
 110  T   G   F   P   R   R   T   Y   E   S   V   E   Q   F   M   S   A   V   G   G  129

4514 ACT AAT AAC GAA ATT GCG AGA TTG CCA ACT TCA GCT GCT ATA AGT AAA TTA TCT GAT TAT 4573
 130  T   N   N   E   I   A   R   L   P   T   S   A   A   I   S   K   L   S   D   Y  149

4574 AAT TTA ATT CCT GGA GAT GTT CTT TAT CTT AAA GCT CAG TTA TAT GCT GAT GCT GAT TTA 4633
 150  N   L   I   P   G   D   V   L   Y   L   K   A   Q   L   Y   A   D   A   D   L  169

4634 CTT GCT CTT GGA ACT ACA AAT ATA TCT CGT TTT TAT AAT GCA TCT AAC GGA TAT ATT 4693
 170  L   A   L   G   T   T   N   I   S   R   F   Y   N   A   S   N   G   Y   I  189

4694 TCT TCA ACA CAA GCT GAA TTT ACT GGG CAA GCT GTA GGA TTT ACG ATA TAC GCA CAG AGA ACT GCA CAA GCT 4753
 190  S   S   T   Q   A   E   F   T   G   Q   A   G   F   T   I   Y   A   Q   R   T   A   Q   A  209

4754 GTA GTT GTT CCA GAA AAC GCA GTA GGA TTT ACG ATA TAC GCA CAG AGA ACT GCA CAA GCT 4813
 210  V   V   V   P   E   N   A   V   G   F   T   I   Y   A   Q   R   T   A   Q   A  229

4814 GGC CAA GGT GGC ATG AGA AAT TTA AGC TTT TCT GAA GTA TCA AGA AAT GGC GGC ATT TCG 4873
 230  G   Q   G   G   M   R   N   L   S   F   S   E   V   S   R   N   G   G   I   S  249
```

FIG. 71

```
4874  AAA CCT GCT GAA TTT GGC GTC AAT GGT ATT CGT GTT AAT TAT ATC TGC GAA TCC GCT TCA  4933
 250   K   P   A   E   F   G   V   N   G   I   R   V   N   Y   I   C   E   S   A   S   269

4934  CCT CCG GAT ATA ATG GTA CTT CCT ACG CAA GCA TCG TCT AAA ACT GGT AAA GTG TTT GGG  4993
 270   P   P   D   I   M   V   L   P   T   Q   A   S   S   K   T   G   K   V   F   G   289

4994  CAA GAA TTT AGA GAA GTT TAA ATTGAGGGACCCTCGGGTTCCCTTTTCTTTATAAATACTATTCAAATAAA  5066
 290   Q   E   F   R   E   V   *                                                        296

5067  GGGCATACA ATG GCT GAT TTA AAA GTA GGT TCA ACA ACT GGA GGC TCT GTC ATT TGG CAT  5127
                M   A   D   L   K   V   G   S   T   T   G   G   S   V   I   W   H    17

5128  CAA GGA AAT TTT CCA TTG AAT CCA GCC GGT GAC GAT GTA CTC TAT AAA TCA TTT AAA ATA  5187
  18   Q   G   N   F   P   L   N   P   A   G   D   D   V   L   Y   K   S   F   K   I    37

5188  TAT TCA GAA TAT AAC AAA CCA CAA GCT GAT AAC GAT TTC GTT TCT AAA GCT AAT GGT  5247
  38   Y   S   E   Y   N   K   P   Q   A   D   N   D   F   V   S   K   A   N   G    57

5248  GGT ACT TAT GCA TCA AAG GTA ACA TTT AAC GGC ATT CAA GTC CCA TAT GCT CCA AAC  5307
  58   G   T   Y   A   S   K   V   T   F   N   A   G   I   Q   V   P   Y   A   P   N    77

5308  ATC ATG AGC CCA TGC GGG ATT TAT GGT GGT AAC GAT GGT GCT ACT TTT GAT AAA GCA  5367
  78   I   M   S   P   C   G   I   Y   G   G   N   D   G   A   T   F   D   K   A    97

5368  AAT ATC GAT ATT GTT TCA TGG TAT GGC GTA GGA TTT AAA TCG TCA TTT GGT TCA ACA GGC  5427
  98   N   I   D   I   V   S   W   Y   G   V   G   F   K   S   S   F   G   S   T   G   117
```

FIG.7J

```
5428  CGA ACT GTT GTA ATT AAT ACA CCC AAT GGT GAT ATT AAC ACA AAA GGT GTT GTC TCG GCA  5487
118    R   T   V   V   I   N   T   R   N   G   D   I   N   T   K   G   V   V   S   A   137

5488  GCT GGT CAA GTA AGA AGT GGT GCG GCT CCT ATA GCA GCC AAT GAC CTT ACT AGA AAG      5547
138    A   G   Q   V   R   S   G   A   A   P   I   A   A   N   D   L   T   R   K      157

5548  GAC TAT GTT GAT GGA GCA ATA AAT ACT GTT ACT GCA AAT GCA AAC TCT AGG GTG CTA CGG  5607
158    D   Y   V   D   G   A   I   N   T   V   T   A   N   A   N   S   R   V   L   R   177

5608  TCT GGT GAC ACC ATG ACA CGG AAT TTA ACA GCG CCA AAC TTT TTC TCG CAG AAT CCT GCA  5667
178    S   G   D   T   M   T   G   N   L   T   A   P   N   F   F   S   Q   N   P   A   197

5668  TCT CAA CCC TCA CAC GTT CCA CGA TTT GAC CAA ATC GTA ATT AAG GAT TCT GTT CAA GAT  5727
198    S   Q   P   S   H   V   P   R   F   D   Q   I   V   I   K   D   S   V   Q   D   217

5728  TTC GGC TAT TAT TAA GAGGACTT ATG GCT ACT TTA AAA CAA ATA CAA TTT AAA AGA AGC AAA 5789
218    F   G   Y   Y   *                M   A   T   L   K   Q   I   Q   F   K   R   S   K    13

5790  ATC GCA GGA ACA CGT CCT GCT TCA GTA TTA GCC GAA GGT GAA TTG GCT ATA AAC TTA      5849
14     I   A   G   T   R   P   A   A   S   V   L   A   E   G   E   L   A   I   N   L      33

5850  AAA GAT AGA ACA ATT TTT ACT AAA GAT GAT TCA GGA AAT ATC GAT CTA GGT TTT GCT      5909
34     K   D   R   T   I   F   T   K   D   D   S   G   N   I   D   L   G   F   A       81

5910  AAA GGC GGG CAA GTT GAT GGC AAC GTT ACT ATT AAC GGA CTT TTG AGA TTA AAT GGC GAT  5969
54     K   G   G   Q   V   D   G   N   V   T   I   N   G   L   L   R   L   N   G   D   73
```

FIG.7K

| | | | | | | | | | | | | | | | | | | | | | |
|---|---|---|---|---|---|---|---|---|---|---|---|---|---|---|---|---|---|---|---|---|---|
| 5970 | TAT | GTA | CAA | ACA | GGT | GGA | ATG | ACT | GTA | AAC | GGA | CCC | ATT | GGT | TCT | ACT | GAT | GGC | GTC | ACT | 6029 |
| 74 | Y | V | Q | T | G | G | M | T | V | N | G | P | I | G | S | T | D | G | V | T | 93 |
| 6030 | GGA | AAA | ATT | TTC | AGA | TCT | ACA | CAG | GGT | TCA | TTT | TAT | GCA | AGA | GCA | ACA | AAC | GAT | ACT | TCA | 6089 |
| 94 | G | K | I | F | R | S | T | Q | G | S | F | Y | A | R | A | T | N | D | T | S | 113 |
| 6090 | AAT | GCC | CAT | TTA | TGG | TTT | GAA | AAT | GCC | GAT | GGC | ACT | GAA | CGT | GGC | GTT | ATA | TAT | CCT | CCC | 6149 |
| 114 | N | A | H | L | W | F | E | N | A | D | G | T | E | R | G | V | I | Y | A | R | 133 |
| 6150 | CCT | CAA | ACT | ACA | GAC | GGT | GAA | ATA | CGC | CTT | AGG | GTT | AGA | CAA | ACA | GGA | ACA | AGC | ACT | TCA | 6209 |
| 134 | P | Q | T | T | D | G | E | I | R | L | R | V | R | Q | T | G | T | S | T | S | 153 |
| 6210 | GCC | AAC | AGT | GAA | TTC | TAT | TTC | CGC | TCT | ATA | AAT | GGA | GGC | GAA | TTT | CAG | GCT | AAC | CGT | ATT | 6269 |
| 154 | A | N | S | E | F | Y | F | R | S | I | N | G | G | E | F | Q | A | N | R | I | 173 |
| 6270 | TTA | GCA | TCA | GAT | TCG | TTA | GTA | ACA | AAA | CGC | ATT | GCG | GTT | GAT | ACC | GTT | ATT | CAT | GAT | GCC | 6329 |
| 174 | L | A | S | D | S | L | V | T | K | R | I | A | V | D | T | V | I | H | D | A | 193 |
| 6330 | AAA | GCA | TTT | GGA | CAA | TAT | GAT | TCT | CAC | TCT | TTG | GTT | AAT | TAT | GTT | TAT | CCT | GGA | ACC | GGT | 6389 |
| 194 | K | A | F | G | Q | Y | D | S | H | S | L | V | N | Y | V | Y | P | G | T | G | 213 |
| 6390 | GAA | ACA | AAT | GGT | GTA | AAC | TAT | CTT | CGT | AAA | GTT | CGC | GCT | AAC | TCC | GGT | ACA | ATT | TAT | 6449 | 911 |
| 214 | E | T | N | G | V | N | Y | L | R | K | V | R | A | K | S | G | T | I | Y | | |
| 6450 | CAT | GAA | ATT | GTT | ACT | GCA | CAA | ACA | GGC | CTG | GCT | GAT | GAA | GTT | TCT | TGG | TCT | GGT | GAT | 6509 | |
| 234 | H | E | I | V | T | A | Q | T | G | L | A | D | E | V | S | W | S | G | D | 253 | |

FIG.7L

| | | | | | | | | | | |
|---|---|---|---|---|---|---|---|---|---|---|
| 6510 | ACA | CCA | GTA | TTT | AAA | CTA | TAC | GGT | ATT | CGT | GAC | GAT | GGC | AGA | ATG | ATT | ATC | CGT | AAT | AGC | 6569 |
| 254 | T | P | V | F | K | L | Y | G | I | R | D | D | G | R | M | I | I | R | N | S | 273 |
| 6570 | CTT | GCA | TTA | GGT | ACA | TTC | ACT | ACA | AAT | TTC | CCG | TCT | AGT | GAT | TAT | GGC | AAC | GTC | GGT | GTA | 6629 |
| 274 | L | A | L | G | T | F | T | T | N | F | P | S | S | D | Y | G | N | V | G | V | 293 |
| 6630 | ATG | GGC | GAT | AAG | TAT | CTT | GTT | CTC | GGC | GAC | ACT | GTA | ACT | GGC | TTG | TCA | TAC | AAA | AAA | ACT | 6689 |
| 294 | M | G | D | K | Y | L | V | L | G | D | T | V | T | G | L | S | Y | K | K | T | 313 |
| 6690 | GGT | GTA | TTT | GAT | CTA | GTT | GGC | GGT | GGA | TAT | TCT | GTT | GCT | TCT | ATT | ACT | CCT | GAC | AGT | TTC | 6749 |
| 314 | G | V | F | D | L | V | G | G | G | Y | S | V | A | S | I | T | P | D | S | F | 333 |
| 6750 | CGT | AGT | ACT | CGT | AAA | GGT | ATA | TTT | GGT | CGT | TCT | GTT | CAA | ACA | CAA | GCT | GAT | AAT | AAC | AAT | 6809 |
| 334 | R | S | T | R | K | G | I | F | G | R | S | V | Q | T | Q | A | D | N | N | N | 353 |
| 6810 | CCT | GGT | ACA | AAT | GCT | GCT | CTC | TTG | TCT | CGT | TCT | GTT | CAA | ACA | CAA | GCT | GGT | AAA | ATG | CAC | TAT | TTC | CGT | GGT | 6869 |
| 354 | P | G | T | N | A | A | L | L | S | R | S | V | Q | T | Q | A | G | K | M | H | Y | F | R | G | 373 |
| 6870 | GAC | GGA | CAA | ACC | CAT | ATC | GGG | TAC | AAT | ACC | CAA | CAA | CAA | GGT | ATG | GAA | ATT | AAC | CCG | GGT | ATT | TTG | AAA | 6929 |
| 374 | D | G | Q | T | H | I | G | Y | N | T | Q | Q | Q | G | M | E | I | N | P | G | I | L | K | 393 |
| 6930 | ACA | GGT | CAG | ATG | AAT | ATC | AAT | AAT | GTA | CAA | TTT | TAC | GCT | GAC | GGA | ACT | ATT | TCT | TCC | ATT | CAA | 6989 |
| 394 | T | G | Q | M | N | I | N | N | V | Q | F | Y | A | D | G | T | I | S | S | I | Q | 413 |
| 6990 | TTG | GTA | ACT | GGC | TCT | AAT | AAT | GTA | CAA | TTT | TAC | GCT | GAC | GGA | ACT | ATT | TCT | TCC | ATT | CAA | 7049 |
| 414 | L | V | T | G | S | N | N | V | Q | F | Y | A | D | G | T | I | S | S | I | Q | 433 |

FIG.7M

```
7050  CCT ATT AAA TTA GAT AAC GAG ATA TTT TTA ACT AAA TCT AAT AAT ACT GCC GGT CTT AAA  7109
434    P   I   K   L   D   N   E   I   F   L   T   K   S   N   N   T   A   G   L   K   453

7110  TTT GGA GCT CCT AGC CAA GTT GAT GGC ACA AGG ACT ATC CAA TGG AAC GGT GGT ACT CGC  7169
454    F   G   A   P   S   Q   V   D   G   T   R   T   I   Q   W   N   G   G   T   R   473

7170  GAA GGA CAG AAT AAA AAC TAT GTG ATT ATT AAA GCA TGG GGT AAC TCA TTT AAT GCC ACT  7229
474    E   G   Q   N   K   N   Y   V   I   I   K   A   W   G   N   S   F   N   A   T   493

7230  GGT GAT AGA TCT CGC GAA ACG GTT TTC CAA GTA TCA GAT AGT CAA GGA TAT TTT TAT  7289
494    G   D   R   S   R   E   T   V   F   Q   V   S   D   S   Q   G   Y   F   Y   513

7290  GCT CAT CGT AAA GCT CCA ACC GGC GAC GAA ACT ATT GGA CGT ATT GAA GCT CAA TTT GCT  7349
514    A   H   R   K   A   P   T   G   D   E   T   I   G   R   I   E   A   Q   F   A   533

7350  GGC GAT GTT TAT GCT AAA GGT ATT ACT ATG TCT AAC GGT TTG TTT GTC CAA GGT GGT TCA AGC  7409
534    G   D   V   Y   A   K   G   I   T   M   S   N   G   L   F   V   Q   G   G   S   553

7410  GCT TTA GCC GGC AAT GTT ACG AAT ATT GGC GGA ACA AAC GCA CTG AGA ATT TGG AAC GCT ATT  7469
554    A   L   A   G   N   V   T   N   I   G   G   T   N   A   L   R   I   W   N   A   I   573

7470  ACT GGA CAA GTT AAA ATT GGC GGT ACT GCA AAC AGT AAC TTT TAT ATT CCA ACC AAT CAA AAT GAA TAT  7529
574    T   G   Q   V   K   I   G   G   T   A   N   S   N   F   Y   I   P   T   N   Q   N   E   Y   593

7530  GGT GCT ATT TTC CGT CGT TCG GAA AGT AAC TTT TAT ATT CCA ACC AAT CAA AAT GAA  7589
594    G   A   I   F   R   R   S   E   S   N   F   Y   I   P   T   N   Q   N   E   613
```

FIG. 7N

```
7590  GGA GAA AGT GGA GAC ATT CAC AGC TCT TTG AGA CCT GTC AGA ATA GGA TTA AAC GAT GGC  7649
614    G   E   S   G   D   I   H   S   S   L   R   P   V   R   I   G   L   N   D   G   633

7650  ATG GTT GGG TTA GGA AGA GAT TCT TTT ATA GTA GAT CAA AAT GCT TTA ACT ACG ATA  7709
634    M   V   G   L   G   R   D   S   F   I   V   D   Q   N   A   L   T   T   I   653

7710  AAC AGT AAC TCT CCC ATT AAT GCC AAC TTT AGA ATG CAA TTG GGG CAG TCC GCA TAC ATT  7769
654    N   S   N   S   R   I   N   A   N   F   R   M   Q   L   G   Q   S   A   Y   I   673

7770  GAT GCA GAA TGT ACT GAT GCT GTT CGC CCG GCC GGT TCA TTT GCT TCC CAG AAT  7829
674    D   A   E   C   T   D   A   V   R   P   A   G   S   F   A   S   Q   N   693

7830  AAT GAA GAC GTC CGT GCC CCG TTC TAT ATG AAT ATT GAT AGA ACT GAT GCT AGT GCA TAT  7889
694    N   E   D   V   R   A   P   F   Y   M   N   I   D   R   T   D   A   S   A   Y   713

7890  GTT CCT ATT TTG AAA CAA CGT TAT GTT CAA GGC AAT TGC TAT TCA TTA GGG ACT TTA  7949
714    V   P   I   L   K   Q   R   Y   V   Q   G   N   C   Y   S   L   G   T   L   733

7950  ATT AAT AAT GGT AAT TTC CGA GTT CAT TAC CAT GGC GGA GAT AAC GGT TCT ACA GGT  8009
734    I   N   N   G   N   F   R   V   H   Y   H   G   G   D   N   G   S   T   G   753

8010  CCA CAG ACT GCT GAT TTT GGA TGG GAA TTT ATT AAA AAC GGT GAT TTT ATT TCA CCT CGC  8069
754    P   Q   T   A   D   F   G   W   E   F   I   K   N   G   D   F   I   S   P   R   773

8070  GAT TTA ATA GCA GGC AAA GTC AGA TTT GAT AGA ACT GGT AAT ATC ACT GGT GGT TCT GGT  8129
774    D   L   I   A   G   K   V   R   F   D   R   T   G   N   I   T   G   G   S   G   793
```

FIG. 70

```
8130  AAT TTT GCT AAC TTA AAC AGT ACA ATT GAA TCA CTT AAA ACT GAT ATC ATG TCG AGT TAC  8180
794    N   F   A   N   L   N   S   T   I   E   S   L   K   T   D   I   M   S   S   Y   813

8190  CCA ATT GGT GCT CCG ATT CCT TGG CCG AGT GAT TCA GTT CCT GCT GGA TTT GCT TTG ATG  8249
814    P   I   G   A   P   I   P   W   P   S   D   S   V   P   A   G   F   A   L   M   833

8250  GAA GGT CAG ACC TTT GAT AAG TCC GCA TAT CCA AAG TTA GCT GTT GCA TAT CCT ACC GGT  8309
834    E   G   Q   T   F   D   K   S   A   Y   P   K   L   A   V   A   Y   P   S   G   853

8310  GTT ATT CCA GAT ATG CGC GGG CAA ACT ATC AAG GGT AAA CCA AGT GGT CGT GCT GTT TTG  8369
854    V   I   P   D   M   R   G   Q   T   I   K   G   K   P   S   G   R   A   V   L   873

8370  AGC GCT GAG GCA GAT GGT GTT AAG GCT CAT AGT GCA TCG GCT TCA AGT ACT GAC          8429
874    S   A   E   A   D   G   V   K   A   H   S   A   S   S   T   D                   893

8430  TTA GGT ACT AAA ACC ACA TCA AGC TTT GAC TAT GGT TCT ACT AGC ACA AAT GGT GAG CAC  8489
894    L   G   T   K   T   T   S   S   F   D   Y   G   T   N   G   E   H               913

8490  GGA CAC ACT CAC TCT GGT AGT GGT ACT GGT GTA GGT GGT AAT AAG ATG TCA TCA TAT GCC  8549
914    G   H   T   H   S   G   S   T   N   G   E   H   S   H   Y   I                   933

8550  GAG GCA TGG AAT GGT ACT GGT GTA GGT GGT AAT AAG ATG TCA TCA TAT GCC ATA TCA TAC  8609
934    E   A   W   N   G   T   G   V   G   G   N   K   M   S   S   Y   A   I   S   Y   953

8610  AGG GCG GGT AGT AAC ACT AAT GCA GCA GGG AAC CAC AGT CAC ACT TTC TCT TTT GGG      8669
954    R   A   G   S   N   T   N   A   A   G   N   H   S   H   T   F   S   F   G       973
```

FIG. 7P

```
8670  ACT AGC AGT GCT GGC GAC CAT TCC CAC TCT GTA GGT ATT GGT GCT CAT ACC CAC ACG GTA  8729
974    T   S   S   A   G   D   H   S   H   S   V   G   I   G   A   H   T   H   T   V   993

8730  GCA ATT GGA TCA CAT GGT CAT ACT ATC ACT GTA AAT AGT ACA GGT AAT ACA GAA AAC ACG  8789
994    A   I   G   S   H   G   H   T   I   T   V   N   S   T   G   N   T   E   N   T   1013

8790  GTT AAA AAC ATT GCT TTT AAC TAT ATC GTT CGT TTA GCA TAA GGAGAGGGCTTCGGCCCTTCTAA  8855
1014   V   K   N   I   A   F   N   Y   I   V   R   L   A   *                            1027
```

FIG.7Q 5,877,279

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 8855 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacteriophage T4

( v i i ) IMMEDIATE SOURCE:
        ( B ) CLONE: TAIL FIBER GENES ( x i ) SEQUENCE DESCRIPTION: SEQ ID NO:1:

```
TAGGAGCCCG  GGAGAATGGC  CGAGATTAAA  AGAGAATTCA  GAGCAGAAGA  TGGTCTGGAC       60

GCAGGTGGTG  ATAAAATAAT  CAACGTAGCT  TTAGCTGATC  GTACCGTAGG  AACTGACGGT      120

GTTAACGTTG  ATTACTTAAT  TCAAGAAAAC  ACAGTTCAAC  AGTATGATCC  AACTCGTGGA      180

TATTTAAAAG  ATTTTGTAAT  CATTTATGAT  AACCGCTTTT  GGGCTGCTAT  AAATGATATT      240

CCAAAACCAG  CAGGAGCTTT  TAATAGCGGA  CGCTGGAGAG  CATTACGTAC  CGATGCTAAC      300

TGGATTACGG  TTTCATCTGG  TTCATATCAA  TTAAAATCTG  GTGAAGCAAT  TTCGGTTAAC      360

ACCGCAGCTG  GAAATGACAT  CACGTTTACT  TTACCATCTT  CTCCAATTGA  TGGTGATACT      420

ATCGTTCTCC  AAGATATTGG  AGGAAAACCT  GGAGTTAACC  AAGTTTTAAT  TGTAGCTCCA      480

GTACAAAGTA  TTGTAAACTT  TAGAGGTGAA  CAGGTACGTT  CAGTACTAAT  GACTCATCCA      540

AAGTCACAGC  TAGTTTTAAT  TTTTAGTAAT  CGTCTGTGGC  AAATGTATGT  TGCTGATTAT      600

AGTAGAGAAG  CTATAGTTGT  AACACCAGCG  AATACTTATC  AAGCGCAATC  CAACGATTTT      660
```

-continued

```
ATCGTACGTA GATTTACTTC TGCTGCACCA ATTAATGTCA AACTTCCAAG ATTTGCTAAT      720
CATGGCGATA TTATTAATTT CGTCGATTTA GATAAACTAA ATCCGCTTTA TCATACAATT      780
GTTACTACAT ACGATGAAAC GACTTCAGTA CAAGAAGTTG GAACTCATTC CATTGAAGGC      840
CGTACATCGA TTGACGGTTT CTTGATGTTT GATGATAATG AGAAATTATG GAGACTGTTT      900
GACGGGGATA GTAAAGCGCG TTTACGTATC ATAACGACTA ATTCAAACAT TCGTCCAAAT      960
GAAGAAGTTA TGGTATTTGG TGCGAATAAC GGAACAACTC AAACAATTGA GCTTAAGCTT     1020
CCAACTAATA TTTCTGTTGG TGATACTGTT AAAATTTCCA TGAATTACAT GAGAAAAGGA     1080
CAAACAGTTA AAATCAAAGC TGCTGATGAA GATAAAATTG CTTCTTCAGT TCAATTGCTG     1140
CAATTCCCAA AACGCTCAGA ATATCCACCT GAAGCTGAAT GGGTTACAGT TCAAGAATTA     1200
GTTTTTAACG ATGAAACTAA TTATGTTCCA GTTTTGGAGC TTGCTTACAT AGAAGATTCT     1260
GATGGAAAAT ATTGGGTTGT ACAGCAAAAC GTTCCAACTG TAGAAAGAGT AGATTCTTTA     1320
AATGATTCTA CTAGAGCAAG ATTAGGCGTA ATTGCTTTAG CTACACAAGC TCAAGCTAAT     1380
GTCGATTTAG AAAATTCTCC ACAAAAGAA TTAGCAATTA CTCCAGAAAC GTTAGCTAAT      1440
CGTACTGCTA CAGAAACTCG CAGAGGTATT GCAAGAATAG CAACTACTGC TCAAGTGAAT     1500
CAGAACACCA CATTCTCTTT TGCTGATGAT ATTATCATCA CTCCTAAAAA GCTGAATGAA     1560
AGAACTGCTA CAGAAACTCG TAGAGGTGTC GCAGAAATTG CTACGCAGCA AGAAACTAAT     1620
GCAGGAACCG ATGATACTAC AATCATCACT CCTAAAAGC TTCAAGCTCG TCAAGGTTCT      1680
GAATCATTAT CTGGTATTGT AACCTTTGTA TCTACTGCAG GTGCTACTCC AGCTTCTAGC     1740
CGTGAATTAA ATGGTACGAA TGTTTATAAT AAAAACACTG ATAATTTAGT TGTTTCACCT     1800
AAAGCTTTGG ATCAGTATAA AGCTACTCCA ACACAGCAAG GTGCAGTAAT TTTAGCAGTT     1860
GAAAGTGAAG TAATTGCTGG ACAAAGTCAG CAAGGATGGG CAAATGCTGT TGTAACGCCA     1920
GAAACGTTAC ATAAAAAGAC ATCAACTGAT GGAAGAATTG GTTTAATTGA AATTGCTACG     1980
CAAAGTGAAG TTAATACAGG AACTGATTAT ACTCGTGCAG TCACTCCTAA AACTTTAAAT     2040
GACCGTAGAG CAACTGAAAG TTTAAGTGGT ATAGCTGAAA TTGCTACACA AGTTGAATTC     2100
GACGCAGGCG TCGACGATAC TCGTATCTCT ACACCATTAA AAATTAAAAC CAGATTTAAT     2160
AGTACTGATC GTACTTCTGT TGTTGCTCTA TCTGGATTAG TTGAATCAGG AACTCTCTGG     2220
GACCATTATA CACTTAATAT TCTTGAAGCA AATGAGACAC AACGTGGTAC ACTTCGTGTA     2280
GCTACGCAGG TCGAAGCTGC TGCGGGAACA TTAGATAATG TTTTAATAAC TCCTAAAAAG     2340
CTTTTAGGTA CTAAATCTAC TGAAGCGCAA GAGGGTGTTA TTAAAGTTGC AACTCAGTCT     2400
GAAACTGTGA CTGGAACGTC AGCAAATACT GCTGTATCTC CAAAAAATTT AAAATGGATT     2460
GCGCAGAGTG AACCTACTTG GGCAGCTACT ACTGCAATAA GAGGTTTTGT TAAAACTTCA     2520
TCTGGTTCAA TTACATTCGT TGGTAATGAT ACAGTCGGTT CTACCCAAGA TTTAGAACTG     2580
TATGAGAAAA ATAGCTATGC GGTATCACCA TATGAATTAA ACCGTGTATT AGCAAATTAT     2640
TTGCCACTAA AAGCAAAAGC TGCTGATACA AATTTATTGG ATGGTCTAGA TTCATCTCAG     2700
TTCATTCGTA GGGATATTGC ACAGACGGTT AATGGTTCAC TAACCTTAAC CCAACAAACG     2760
AATCTGAGTG CCCCTCTTGT ATCATCTAGT ACTGGTGAAT TGGTGGTTC ATTGGCCGCT      2820
AATAGAACAT TTACCATCCG TAATACAGGA GCCCCGACTA GTATCGTTTT CGAAAAGGT      2880
CCTGCATCCG GGGCAAATCC TGCACAGTCA ATGAGTATTC GTGTATGGGG TAACCAATTT     2940
GGCGGCGGTA GTGATACGAC CCGTTCGACA GTGTTTGAAG TTGGCGATGA CACATCTCAT     3000
CACTTTTATT CTCAACGTAA TAAAGACGGT AATATAGCGT TTAACATTAA TGGTACTGTA     3060
```

| ATGCCAATAA | ACATTAATGC | TTCCGGTTTG | ATGAATGTGA | ATGGCACTGC | AACATTCGGT | 3120 |
| CGTTCAGTTA | CAGCCAATGG | TGAATTCATC | AGCAAGTCTG | CAAATGCTTT | TAGAGCAATA | 3180 |
| AACGGTGATT | ACGGATTCTT | TATTCGTAAT | GATGCCTCTA | ATACCTATTT | TTTGCTCACT | 3240 |
| GCAGCCGGTG | ATCAGACTGG | TGGTTTTAAT | GGATTACGCC | CATTATTAAT | TAATAATCAA | 3300 |
| TCCGGTCAGA | TTACAATTGG | TGAAGGCTTA | ATCATTGCCA | AAGGTGTTAC | TATAAATTCA | 3360 |
| GGCGGTTTAA | CTGTTAACTC | GAGAATTCGT | TCTCAGGGTA | CTAAAACATC | TGATTTATAT | 3420 |
| ACCCGTGCGC | CAACATCTGA | TACTGTAGGA | TTCTGGTCAA | TCGATATTAA | TGATTCAGCC | 3480 |
| ACTTATAACC | AGTTCCCGGG | TTATTTTAAA | ATGGTTGAAA | AAACTAATGA | AGTGACTGGG | 3540 |
| CTTCCATACT | TAGAACGTGG | CGAAGAAGTT | AAATCTCCTG | GTACACTGAC | TCAGTTTGGT | 3600 |
| AACACACTTG | ATTCGCTTTA | CCAAGATTGG | ATTACTTATC | CAACGACGCC | AGAAGCGCGT | 3660 |
| ACCACTCGCT | GGACACGTAC | ATGGCAGAAA | ACCAAAAACT | CTTGGTCAAG | TTTTGTTCAG | 3720 |
| GTATTTGACG | GAGGTAACCC | TCCTCAACCA | TCTGATATCG | GTGCTTTACC | ATCTGATAAT | 3780 |
| GCTACAATGG | GGAATCTTAC | TATTCGTGAT | TTCTTGCGAA | TTGGTAATGT | TCGCATTGTT | 3840 |
| CCTGACCCAG | TGAATAAAAC | GGTTAAATTT | GAATGGGTTG | AATAAGAGGT | ATTATGGAAA | 3900 |
| AATTTATGGC | CGAGATTTGG | ACAAGGATAT | GTCCAAACGC | CATTTTATCG | GAAAGTAATT | 3960 |
| CAGTAAGATA | TAAAATAAGT | ATAGCGGGTT | CTTGCCCGCT | TTCTACAGCA | GGACCATCAT | 4020 |
| ATGTTAAATT | TCAGGATAAT | CCTGTAGGAA | GTCAAACATT | TAGGCGCAGG | CCTTCATTTA | 4080 |
| AGAGTTTTTG | ACCCTTCCAC | CGGAGCATTA | GTTGATAGTA | AGTCATATGC | TTTTTCGACT | 4140 |
| TCAAATGATA | CTACATCAGC | TGCTTTTGTT | AGTTTTCATG | AATTCTTTGA | CGAATAATCG | 4200 |
| AATTGTTGCT | ATATTAACTA | GTGGAAAGGT | TAATTTTCCT | CCTGAAGTAG | TATCTTGGTT | 4260 |
| AAGAACCGCC | GGAACGTCTG | CCTTTCCATC | TGATTCTATA | TTGTCAAGAT | TGACGTATC | 4320 |
| ATATGCTGCT | TTTTATACTT | CTTCTAAAAG | AGCTATCGCA | TTAGAGCATG | TTAAACTGAG | 4380 |
| TAATAGAAAA | AGCACAGATG | ATTATCAAAC | TATTTTAGAT | GTTGTATTTG | ACAGTTTAGA | 4440 |
| AGATGTAGGA | GCTACCGGGT | TTCCAAGAAG | AACGTATGAA | AGTGTTGAGC | AATTCATGTC | 4500 |
| GGCAGTTGGT | GGAACTAATA | ACGAAATTGC | GAGATTGCCA | ACTTCAGCTG | CTATAAGTAA | 4560 |
| ATTATCTGAT | TATAATTTAA | TTCCTGGAGA | TGTTCTTTAT | CTTAAAGCTC | AGTTATATGC | 4620 |
| TGATGCTGAT | TTACTTGCTC | TTGGAACTAC | AAATATATCT | ATCCGTTTTT | ATAATGCATC | 4680 |
| TAACGGATAT | ATTTCTTCAA | CACAAGCTGA | ATTTACTGGG | CAAGCTGGGT | CATGGGAATT | 4740 |
| AAAGGAAGAT | TATGTAGTTG | TTCCAGAAAA | CGCAGTAGGA | TTTACGATAT | ACGCACAGAG | 4800 |
| AACTGCACAA | GCTGGCCAAG | GTGGCATGAG | AAATTTAAGC | TTTTCTGAAG | TATCAAGAAA | 4860 |
| TGGCGGCATT | TCGAAACCTG | CTGAATTTGG | CGTCAATGGT | ATTCGTGTTA | ATTATATCTG | 4920 |
| CGAATCCGCT | TCACCTCCGG | ATATAATGGT | ACTTCCTACG | CAAGCATCGT | CTAAAACTGG | 4980 |
| TAAAGTGTTT | GGGCAAGAAT | TTAGAGAAGT | TTAAATTGAG | GGACCCTTCG | GGTTCCCTTT | 5040 |
| TTCTTTATAA | ATACTATTCA | AATAAGGGG | CATACAATGG | CTGATTAAA | AGTAGGTTCA | 5100 |
| ACAACTGGAG | GCTCTGTCAT | TTGGCATCAA | GGAAATTTTC | CATTGAATCC | AGCCGGTGAC | 5160 |
| GATGTACTCT | ATAAATCATT | TAAATATAT | TCAGAATATA | ACAAACCACA | AGCTGCTGAT | 5220 |
| AACGATTTCG | TTTCTAAAGC | TAATGGTGGT | ACTTATGCAT | CAAAGGTAAC | ATTTAACGCT | 5280 |
| GGCATTCAAG | TCCCATATGC | TCCAAACATC | ATGAGCCCAT | GCGGGATTTA | TGGGGTAAC | 5340 |
| GGTGATGGTG | CTACTTTTGA | TAAAGCAAAT | ATCGATATTG | TTTCATGGTA | TGGCGTAGGA | 5400 |
| TTTAAATCGT | CATTTGGTTC | AACAGGCCGA | ACTGTTGTAA | TTAATACACG | CAATGGTGAT | 5460 |

```
ATTAACACAA  AAGGTGTTGT  GTCGGCAGCT  GGTCAAGTAA  GAAGTGGTGC  GGCTGCTCCT   5520

ATAGCAGCGA  ATGACCTTAC  TAGAAAGGAC  TATGTTGATG  GAGCAATAAA  TACTGTTACT   5580

GCAAATGCAA  ACTCTAGGGT  GCTACGGTCT  GGTGACACCA  TGACAGGTAA  TTTAACAGCG   5640

CCAAACTTTT  TCTCGCAGAA  TCCTGCATCT  CAACCCTCAC  ACGTTCCACG  ATTTGACCAA   5700

ATCGTAATTA  AGGATTCTGT  TCAAGATTTC  GGCTATTATT  AAGAGGACTT  ATGGCTACTT   5760

TAAAACAAAT  ACAATTTAAA  AGAAGCAAAA  TCGCAGGAAC  ACGTCCTGCT  GCTTCAGTAT   5820

TAGCCGAAGG  TGAATTGGCT  ATAAACTTAA  AAGATAGAAC  AATTTTTACT  AAAGATGATT   5880

CAGGAAATAT  CATCGATCTA  GGTTTTGCTA  AAGGCGGGCA  AGTTGATGGC  AACGTTACTA   5940

TTAACGGACT  TTTGAGATTA  AATGGCGATT  ATGTACAAAC  AGGTGGAATG  ACTGTAAACG   6000

GACCCATTGG  TTCTACTGAT  GGCGTCACTG  GAAAAATTTT  CAGATCTACA  CAGGGTTCAT   6060

TTTATGCAAG  AGCAACAAAC  GATACTTCAA  ATGCCCATTT  ATGGTTTGAA  AATGCCGATG   6120

GCACTGAACG  TGGCGTTATA  TATGCTCGCC  CTCAAACTAC  AACTGACGGT  GAAATACGCC   6180

TTAGGGTTAG  ACAAGGAACA  GGAAGCACTG  CCAACAGTGA  ATTCTATTTC  CGCTCTATAA   6240

ATGGAGGCGA  ATTTCAGGCT  AACCGTATTT  TAGCATCAGA  TTCGTTAGTA  ACAAAACGCA   6300

TTGCGGTTGA  TACCGTTATT  CATGATGCCA  AGCATTTGG   ACAATATGAT  TCTCACTCTT   6360

TGGTTAATTA  TGTTTATCCT  GGAACCGGTG  AAACAAATGG  TGTAAACTAT  CTTCGTAAAG   6420

TTCGCGCTAA  GTCCGGTGGT  ACAATTTATC  ATGAAATTGT  TACTGCACAA  ACAGGCCTGG   6480

CTGATGAAGT  TTCTTGGTGG  TCTGGTGATA  CACCAGTATT  TAAACTATAC  GGTATTCGTG   6540

ACGATGGCAG  AATGATTATC  CGTAATAGCC  TTGCATTAGG  TACATTCACT  ACAAATTTCC   6600

CGTCTAGTGA  TTATGGCAAC  GTCGGTGTAA  TGGGCGATAA  GTATCTTGTT  CTCGGCGACA   6660

CTGTAACTGG  CTTGTCATAC  AAAAAAACTG  GTGTATTTGA  TCTAGTTGGC  GGTGGATATT   6720

CTGTTGCTTC  TATTACTCCT  GACAGTTTCC  GTAGTACTCG  TAAAGGTATA  TTTGGTCGTT   6780

CTGAGGACCA  AGGCGCAACT  TGGATAATGC  CTGGTACAAA  TGCTGCTCTC  TTGTCTGTTC   6840

AAACACAAGC  TGATAATAAC  AATGCTGGAG  ACGGACAAAC  CCATATCGGG  TACAATGCTG   6900

GCGGTAAAAT  GAACCACTAT  TTCCGTGGTA  CAGGTCAGAT  GAATATCAAT  ACCCAACAAG   6960

GTATGGAAAT  TAACCCGGGT  ATTTTGAAAT  TGGTAACTGG  CTCTAATAAT  GTACAATTTT   7020

ACGCTGACGG  AACTATTTCT  TCCATTCAAC  CTATTAAATT  AGATAACGAG  ATATTTTTAA   7080

CTAAATCTAA  TAATACTGCG  GGTCTTAAAT  TTGGAGCTCC  TAGCCAAGTT  GATGGCACAA   7140

GGACTATCCA  ATGGAACGGT  GGTACTCGCG  AAGGACAGAA  TAAAAACTAT  GTGATTATTA   7200

AAGCATGGGG  TAACTCATTT  AATGCCACTG  GTGATAGATC  TCGCGAAACG  GTTTTCCAAG   7260

TATCAGATAG  TCAAGGATAT  TATTTTTATG  CTCATCGTAA  AGCTCCAACC  GGCGACGAAA   7320

CTATTGGACG  TATTGAAGCT  CAATTTGCTG  GGGATGTTTA  TGCTAAAGGT  ATTATTGCCA   7380

ACGGAAATTT  TAGAGTTGTT  GGGTCAAGCG  CTTTAGCCGG  CAATGTTACT  ATGTCTAACG   7440

GTTTGTTTGT  CCAAGGTGGT  TCTTCTATTA  CTGGACAAGT  TAAAATTGGC  GGAACAGCAA   7500

ACGCACTGAG  AATTTGGAAC  GCTGAATATG  GTGCTATTTT  CCGTCGTTCG  GAAAGTAACT   7560

TTTATATTAT  TCCAACCAAT  CAAAATGAAG  GAGAAAGTGG  AGACATTCAC  AGCTCTTTGA   7620

GACCTGTGAG  AATAGGATTA  AACGATGGCA  TGGTTGGGTT  AGGAAGAGAT  TCTTTTATAG   7680

TAGATCAAAA  TAATGCTTTA  ACTACGATAA  ACAGTAACTC  TCGCATTAAT  GCCAACTTTA   7740

GAATGCAATT  GGGGCAGTCG  GCATACATTG  ATGCAGAATG  TACTGATGCT  GTTCGCCCGG   7800

CGGGTGCAGG  TTCATTTGCT  TCCCAGAATA  ATGAAGACGT  CCGTGCGCCG  TTCTATATGA   7860
```

-continued

```
ATATTGATAG AACTGATGCT AGTGCATATG TTCCTATTTT GAAACAACGT TATGTTCAAG    7920
GCAATGGCTG CTATTCATTA GGGACTTTAA TTAATAATGG TAATTTCCGA GTTCATTACC    7980
ATGGCGGCGG AGATAACGGT TCTACAGGTC CACAGACTGC TGATTTTGGA TGGGAATTTA    8040
TTAAAAACGG TGATTTTATT TCACCTCGCG ATTAATAGC AGGCAAAGTC AGATTTGATA     8100
GAACTGGTAA TATCACTGGT GGTTCTGGTA ATTTGCTAA CTTAAACAGT ACAATTGAAT     8160
CACTTAAAAC TGATATCATG TCGAGTTACC CAATTGGTGC TCCGATTCCT TGGCCGAGTG    8220
ATTCAGTTCC TGCTGGATTT GCTTTGATGG AAGGTCAGAC CTTTGATAAG TCCGCATATC    8280
CAAAGTTAGC TGTTGCATAT CCTAGCGGTG TTATTCCAGA TATGCGCGGG CAAACTATCA    8340
AGGGTAAACC AAGTGGTCGT GCTGTTTTGA GCGCTGAGGC AGATGGTGTT AAGGCTCATA    8400
GCCATAGTGC ATCGGCTTCA AGTACTGACT TAGGTACTAA AACCACATCA AGCTTTGACT    8460
ATGGTACGAA GGGAACTAAC AGTACGGGTG GACACACTCA CTCTGGTAGT GGTTCTACTA    8520
GCACAAATGG TGAGCACAGC CACTACATCG AGGCATGGAA TGGTACTGGT GTAGGTGGTA    8580
ATAAGATGTC ATCATATGCC ATATCATACA GGGCGGGTGG GAGTAACACT AATGCAGCAG    8640
GGAACCACAG TCACACTTTC TCTTTTGGGA CTAGCAGTGC TGGCGACCAT TCCCACTCTG    8700
TAGGTATTGG TGCTCATACC CACACGGTAG CAATTGGATC ACATGGTCAT ACTATCACTG    8760
TAAATAGTAC AGGTAATACA GAAAACACGG TTAAAAACAT TGCTTTTAAC TATATCGTTC    8820
GTTTAGCATA AGGAGAGGGG CTTCGGCCCT TCTAA                               8855
```

(2) INFORMATION FOR SEQ ID NO:2:

(i) SEQUENCE CHARACTERISTICS:
  (A) LENGTH: 1289 amino acids
  (B) TYPE: amino acid
  (D) TOPOLOGY: linear (ii) MOLECULE TYPE: protein (vi) ORIGINAL SOURCE:
  (A) ORGANISM: Bacteriophage T4

(vii) IMMEDIATE SOURCE:
  (B) CLONE: p34 amino acid (xi) SEQUENCE DESCRIPTION: SEQ ID NO:2:

```
Met Ala Glu Ile Lys Arg Glu Phe Arg Ala Glu Asp Gly Leu Asp Ala
 1               5                  10                  15

Gly Gly Asp Lys Ile Ile Asn Val Ala Leu Ala Asp Arg Thr Val Gly
                20                  25                  30

Thr Asp Gly Val Asn Val Asp Tyr Leu Ile Gln Glu Asn Thr Val Gln
            35                  40                  45

Gln Tyr Asp Pro Thr Arg Gly Tyr Leu Lys Asp Phe Val Ile Ile Tyr
        50                  55                  60

Asp Asn Arg Phe Trp Ala Ala Ile Asn Asp Ile Pro Lys Pro Ala Gly
 65                 70                  75                  80

Ala Phe Asn Ser Gly Arg Trp Arg Ala Leu Arg Thr Asp Ala Asn Trp
                85                  90                  95

Ile Thr Val Ser Ser Gly Ser Tyr Gln Leu Lys Ser Gly Glu Ala Ile
                    100                 105                 110

Ser Val Asn Thr Ala Ala Gly Asn Asp Ile Thr Phe Thr Leu Pro Ser
                115                 120                 125

Ser Pro Ile Asp Gly Asp Thr Ile Val Leu Gln Asp Ile Gly Gly Lys
            130                 135                 140
```

-continued

| | | | | | | | | | | | | | | | |
|---|---|---|---|---|---|---|---|---|---|---|---|---|---|---|---|
|Pro<br>145|Gly|Val|Asn|Gln<br>150|Val|Leu|Ile|Val|Ala<br>155|Pro|Val|Gln|Ser|Ile|Val<br>160|
|Asn|Phe|Arg|Gly|Glu<br>165|Gln|Val|Arg|Ser|Val<br>170|Leu|Met|Thr|His|Pro<br>175|Lys|
|Ser|Gln|Leu|Val<br>180|Leu|Ile|Phe|Ser|Asn<br>185|Arg|Leu|Trp|Gln|Met<br>190|Tyr|Val|
|Ala|Asp|Tyr<br>195|Ser|Arg|Glu|Ala|Ile<br>200|Val|Val|Thr|Pro|Ala<br>205|Asn|Thr|Tyr|
|Gln|Ala<br>210|Gln|Ser|Asn|Asp|Phe<br>215|Ile|Val|Arg|Arg|Phe<br>220|Thr|Ser|Ala|Ala|
|Pro<br>225|Ile|Asn|Val|Lys|Leu<br>230|Pro|Arg|Phe|Ala|Asn<br>235|His|Gly|Asp|Ile|Ile<br>240|
|Asn|Phe|Val|Asp|Leu<br>245|Asp|Lys|Leu|Asn|Pro<br>250|Leu|Tyr|His|Thr|Ile<br>255|Val|
|Thr|Thr|Tyr|Asp<br>260|Glu|Thr|Thr|Ser|Val<br>265|Gln|Glu|Val|Gly|Thr<br>270|His|Ser|
|Ile|Glu|Gly|Arg<br>275|Thr|Ser|Ile|Asp|Gly<br>280|Phe|Leu|Met|Phe<br>285|Asp|Asp|Asn|
|Glu|Lys|Leu<br>290|Trp|Arg|Leu|Phe|Asp<br>295|Gly|Asp|Ser|Lys<br>300|Ala|Arg|Leu|Arg|
|Ile<br>305|Ile|Thr|Thr|Asn|Ser<br>310|Asn|Ile|Arg|Pro|Asn<br>315|Glu|Glu|Val|Met|Val<br>320|
|Phe|Gly|Ala|Asn|Asn<br>325|Gly|Thr|Thr|Gln|Thr<br>330|Ile|Glu|Leu|Lys|Leu<br>335|Pro|
|Thr|Asn|Ile|Ser<br>340|Val|Gly|Asp|Thr|Val<br>345|Lys|Ile|Ser|Met|Asn<br>350|Tyr|Met|
|Arg|Lys|Gly<br>355|Gln|Thr|Val|Lys|Ile<br>360|Lys|Ala|Ala|Asp|Glu<br>365|Asp|Lys|Ile|
|Ala|Ser|Ser|Val<br>370|Gln|Leu|Leu|Gln<br>375|Phe|Pro|Lys|Arg|Ser<br>380|Glu|Tyr|Pro|
|Pro<br>385|Glu|Ala|Glu|Trp|Val<br>390|Thr|Val|Gln|Glu|Leu<br>395|Val|Phe|Asn|Asp|Glu<br>400|
|Thr|Asn|Tyr|Val|Pro<br>405|Val|Leu|Glu|Leu|Ala<br>410|Tyr|Ile|Glu|Asp|Ser<br>415|Asp|
|Gly|Lys|Tyr|Trp<br>420|Val|Val|Gln|Gln|Asn<br>425|Val|Pro|Thr|Val|Glu<br>430|Arg|Val|
|Asp|Ser|Leu|Asn<br>435|Asp|Ser|Thr|Arg|Ala<br>440|Arg|Leu|Gly|Val|Ile<br>445|Ala|Leu|
|Ala|Thr<br>450|Gln|Ala|Gln|Ala|Asn<br>455|Val|Asp|Leu|Glu|Asn<br>460|Ser|Pro|Gln|Lys|
|Glu<br>465|Leu|Ala|Ile|Thr|Pro<br>470|Glu|Thr|Leu|Ala|Asn<br>475|Arg|Thr|Ala|Thr|Glu<br>480|
|Thr|Arg|Arg|Gly|Ile<br>485|Ala|Arg|Ile|Ala|Thr<br>490|Thr|Ala|Gln|Val|Asn<br>495|Gln|
|Asn|Thr|Thr|Phe|Ser<br>500|Phe|Ala|Asp|Asp|Ile<br>505|Ile|Ile|Thr|Pro|Lys<br>510|Lys|
|Leu|Asn|Glu|Arg<br>515|Thr|Ala|Thr|Glu<br>520|Thr|Arg|Arg|Gly|Val<br>525|Ala|Glu|Ile|
|Ala|Thr|Gln|Gln<br>530|Glu|Thr|Asn|Ala|Gly<br>535|Thr|Asp|Asp|Thr<br>540|Thr|Ile|Ile|
|Thr|Pro|Lys|Lys<br>545|Leu|Gln|Ala|Arg|Gln<br>550|Gly|Ser|Glu|Ser<br>555|Leu|Ser|Gly<br>560|
|Ile|Val|Thr|Phe|Val<br>565|Ser|Thr|Ala|Gly|Ala<br>570|Thr|Pro|Ala|Ser|Ser<br>575|Arg|

```
Glu  Leu  Asn  Gly  Thr  Asn  Val  Tyr  Asn  Lys  Asn  Thr  Asp  Asn  Leu  Val
               580                     585                    590

Val  Ser  Pro  Lys  Ala  Leu  Asp  Gln  Tyr  Lys  Ala  Thr  Pro  Thr  Gln  Gln
          595                    600                    605

Gly  Ala  Val  Ile  Leu  Ala  Val  Glu  Ser  Glu  Val  Ile  Ala  Gly  Gln  Ser
     610                     615                    620

Gln  Gln  Gly  Trp  Ala  Asn  Ala  Val  Val  Thr  Pro  Glu  Thr  Leu  His  Lys
625                      630                    635                         640

Lys  Thr  Ser  Thr  Asp  Gly  Arg  Ile  Gly  Leu  Ile  Glu  Ile  Ala  Thr  Gln
                    645                    650                         655

Ser  Glu  Val  Asn  Thr  Gly  Thr  Asp  Tyr  Thr  Arg  Ala  Val  Thr  Pro  Lys
               660                    665                         670

Thr  Leu  Asn  Asp  Arg  Arg  Ala  Thr  Glu  Ser  Leu  Ser  Gly  Ile  Ala  Glu
          675                         680                    685

Ile  Ala  Thr  Gln  Val  Glu  Phe  Asp  Ala  Gly  Val  Asp  Asp  Thr  Arg  Ile
     690                     695                         700

Ser  Thr  Pro  Leu  Lys  Ile  Lys  Thr  Arg  Phe  Asn  Ser  Thr  Asp  Arg  Thr
705                      710                    715                         720

Ser  Val  Val  Ala  Leu  Ser  Gly  Leu  Val  Glu  Ser  Gly  Thr  Leu  Trp  Asp
                    725                    730                    735

His  Tyr  Thr  Leu  Asn  Ile  Leu  Glu  Ala  Asn  Glu  Thr  Gln  Arg  Gly  Thr
               740                    745                    750

Leu  Arg  Val  Ala  Thr  Gln  Val  Glu  Ala  Ala  Ala  Gly  Thr  Leu  Asp  Asn
          755                    760                    765

Val  Leu  Ile  Thr  Pro  Lys  Lys  Leu  Leu  Gly  Thr  Lys  Ser  Thr  Glu  Ala
     770                     775                    780

Gln  Glu  Gly  Val  Ile  Lys  Val  Ala  Thr  Gln  Ser  Glu  Thr  Val  Thr  Gly
785                      790                    795                         800

Thr  Ser  Ala  Asn  Thr  Ala  Val  Ser  Pro  Lys  Asn  Leu  Lys  Trp  Ile  Ala
                    805                    810                         815

Gln  Ser  Glu  Pro  Thr  Trp  Ala  Ala  Thr  Thr  Ala  Ile  Arg  Gly  Phe  Val
               820                    825                    830

Lys  Thr  Ser  Ser  Gly  Ser  Ile  Thr  Phe  Val  Gly  Asn  Asp  Thr  Val  Gly
          835                    840                    845

Ser  Thr  Gln  Asp  Leu  Glu  Leu  Tyr  Glu  Lys  Asn  Ser  Tyr  Ala  Val  Ser
     850                     855                    860

Pro  Tyr  Glu  Leu  Asn  Arg  Val  Leu  Ala  Asn  Tyr  Leu  Pro  Leu  Lys  Ala
865                      870                    875                         880

Lys  Ala  Ala  Asp  Thr  Asn  Leu  Leu  Asp  Gly  Leu  Asp  Ser  Ser  Gln  Phe
                    885                    890                         895

Ile  Arg  Arg  Asp  Ile  Ala  Gln  Thr  Val  Asn  Gly  Ser  Leu  Thr  Leu  Thr
               900                    905                    910

Gln  Gln  Thr  Asn  Leu  Ser  Ala  Pro  Leu  Val  Ser  Ser  Thr  Gly  Glu
          915                    920                    925

Phe  Gly  Gly  Ser  Leu  Ala  Ala  Asn  Arg  Thr  Phe  Thr  Ile  Arg  Asn  Thr
     930                     935                    940

Gly  Ala  Pro  Thr  Ser  Ile  Val  Phe  Glu  Lys  Gly  Pro  Ala  Ser  Gly  Ala
945                      950                    955                         960

Asn  Pro  Ala  Gln  Ser  Met  Ser  Ile  Arg  Val  Trp  Gly  Asn  Gln  Phe  Gly
                    965                    970                         975

Gly  Gly  Ser  Asp  Thr  Thr  Arg  Ser  Thr  Val  Phe  Glu  Val  Gly  Asp  Asp
               980                    985                    990

Thr  Ser  His  His  Phe  Tyr  Ser  Gln  Arg  Asn  Lys  Asp  Gly  Asn  Ile  Ala
```

-continued

```
                    995                        1000                        1005
    Phe  Asn  Ile  Asn  Gly  Thr  Val  Met  Pro  Ile  Asn  Ile  Asn  Ala  Ser  Gly
         1010                       1015                      1020

Leu  Met  Asn  Val  Asn  Gly  Thr  Ala  Thr  Phe  Gly  Arg  Ser  Val  Thr  Ala
    1025                     1030                        1035                   1040

Asn  Gly  Glu  Phe  Ile  Ser  Lys  Ser  Ala  Asn  Ala  Phe  Arg  Ala  Ile  Asn
                        1045                      1050                      1055

Gly  Asp  Tyr  Gly  Phe  Phe  Ile  Arg  Asn  Asp  Ala  Ser  Asn  Thr  Tyr  Phe
                   1060                      1065                      1070

Leu  Leu  Thr  Ala  Ala  Gly  Asp  Gln  Thr  Gly  Gly  Phe  Asn  Gly  Leu  Arg
              1075                      1080                      1085

Pro  Leu  Leu  Ile  Asn  Asn  Gln  Ser  Gly  Gln  Ile  Thr  Ile  Gly  Glu  Gly
         1090                       1095                      1100

Leu  Ile  Ile  Ala  Lys  Gly  Val  Thr  Ile  Asn  Ser  Gly  Gly  Leu  Thr  Val
    1105                     1110                        1115                   1120

Asn  Ser  Arg  Ile  Arg  Ser  Gln  Gly  Thr  Lys  Thr  Ser  Asp  Leu  Tyr  Thr
                        1125                      1130                      1135

Arg  Ala  Pro  Thr  Ser  Asp  Thr  Val  Gly  Phe  Trp  Ser  Ile  Asp  Ile  Asn
                   1140                      1145                      1150

Asp  Ser  Ala  Thr  Tyr  Asn  Gln  Phe  Pro  Gly  Tyr  Phe  Lys  Met  Val  Glu
              1155                      1160                      1165

Lys  Thr  Asn  Glu  Val  Thr  Gly  Leu  Pro  Tyr  Leu  Glu  Arg  Gly  Glu  Glu
         1170                       1175                      1180

Val  Lys  Ser  Pro  Gly  Thr  Leu  Thr  Gln  Phe  Gly  Asn  Thr  Leu  Asp  Ser
    1185                     1190                        1195                   1200

Leu  Tyr  Gln  Asp  Trp  Ile  Thr  Tyr  Pro  Thr  Thr  Pro  Glu  Ala  Arg  Thr
                        1205                      1210                      1215

Thr  Arg  Trp  Thr  Arg  Thr  Trp  Gln  Lys  Thr  Lys  Asn  Ser  Trp  Ser  Ser
                   1220                      1225                      1230

Phe  Val  Gln  Val  Phe  Asp  Gly  Gly  Asn  Pro  Pro  Gln  Pro  Ser  Asp  Ile
              1235                      1240                      1245

Gly  Ala  Leu  Pro  Ser  Asp  Asn  Ala  Thr  Met  Gly  Asn  Leu  Thr  Ile  Arg
         1250                       1255                      1260

Asp  Phe  Leu  Arg  Ile  Gly  Asn  Val  Arg  Ile  Val  Pro  Asp  Pro  Val  Asn
    1265                     1270                        1275                   1280

Lys  Thr  Val  Lys  Phe  Glu  Trp  Val  Glu
                        1285
```

( 2 ) INFORMATION FOR SEQ ID NO:3:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Bacteriophage T4

( v i i ) IMMEDIATE SOURCE:
        ( B ) CLONE: ORF X amino acid ( x i ) SEQUENCE DESCRIPTION: SEQ ID NO:3:

```
    Met  Glu  Lys  Phe  Met  Ala  Glu  Ile  Trp  Thr  Arg  Ile  Cys  Pro  Asn  Ala
    1                   5                        10                         15

Ile  Leu  Ser  Glu  Ser  Asn  Ser  Val  Arg  Tyr  Lys  Ile  Ser  Ile  Ala  Gly
                   20                        25                        30
```

|   |   |   |   |   |   |   |   |   |   |   |   |   |   |   |
|---|---|---|---|---|---|---|---|---|---|---|---|---|---|---|
| Ser | Cys | Pro<br>35 | Leu | Ser | Thr | Ala | Gly<br>40 | Pro | Ser | Tyr | Val | Lys<br>45 | Phe | Gln | Asp |
| Asn | Pro<br>50 | Val | Gly | Ser | Gln | Thr<br>55 | Phe | Arg | Arg | Arg | Pro<br>60 | Ser | Phe | Lys | Ser |
| Phe<br>65 |

(2) INFORMATION FOR SEQ ID NO:4:

(i) SEQUENCE CHARACTERISTICS:
        (A) LENGTH: 295 amino acids
        (B) TYPE: amino acid
        (D) TOPOLOGY: linear (ii) MOLECULE TYPE: protein (vi) ORIGINAL SOURCE:
        (A) ORGANISM: Bacteriophage T4

(vii) IMMEDIATE SOURCE:
        (B) CLONE: p35 amino acid (xi) SEQUENCE DESCRIPTION: SEQ ID NO:4:

|   |   |   |   |   |   |   |   |   |   |   |   |   |   |   |   |
|---|---|---|---|---|---|---|---|---|---|---|---|---|---|---|---|
| Met<br>1 | Leu | Phe | Arg | Leu<br>5 | Gln | Met | Ile | Leu | His<br>10 | Gln | Leu | Leu | Leu | Leu<br>15 | Val |
| Phe | Met | Asn | Ser<br>20 | Leu | Thr | Asn | Asn | Arg<br>25 | Ile | Val | Ala | Ile | Leu<br>30 | Thr | Ser |
| Gly | Lys | Val<br>35 | Asn | Phe | Pro | Pro | Glu<br>40 | Val | Val | Ser | Trp | Leu<br>45 | Arg | Thr | Ala |
| Gly | Thr<br>50 | Ser | Ala | Phe | Pro | Ser<br>55 | Asp | Ser | Ile | Leu | Ser<br>60 | Arg | Phe | Asp | Val |
| Ser<br>65 | Tyr | Ala | Ala | Phe | Tyr<br>70 | Thr | Ser | Ser | Lys | Arg<br>75 | Ala | Ile | Ala | Leu | Glu<br>80 |
| His | Val | Lys | Leu | Ser<br>85 | Asn | Arg | Lys | Ser | Thr<br>90 | Asp | Asp | Tyr | Gln | Thr<br>95 | Ile |
| Leu | Asp | Val | Val<br>100 | Phe | Asp | Ser | Leu | Glu<br>105 | Asp | Val | Gly | Ala | Thr<br>110 | Gly | Phe |
| Pro | Arg | Arg<br>115 | Thr | Tyr | Glu | Ser | Val<br>120 | Glu | Gln | Phe | Met | Ser<br>125 | Ala | Val | Gly |
| Gly | Thr<br>130 | Asn | Asn | Glu | Ile | Ala<br>135 | Arg | Leu | Pro | Thr | Ser<br>140 | Ala | Ala | Ile | Ser |
| Lys<br>145 | Leu | Ser | Asp | Tyr | Asn<br>150 | Leu | Ile | Pro | Gly | Asp<br>155 | Val | Leu | Tyr | Leu | Lys<br>160 |
| Ala | Gln | Leu | Tyr | Ala<br>165 | Asp | Ala | Asp | Leu | Leu<br>170 | Ala | Leu | Gly | Thr | Thr<br>175 | Asn |
| Ile | Ser | Ile | Arg<br>180 | Phe | Tyr | Asn | Ala | Ser<br>185 | Asn | Gly | Tyr | Ile | Ser<br>190 | Ser | Thr |
| Gln | Ala | Glu<br>195 | Phe | Thr | Gly | Gln | Ala<br>200 | Gly | Ser | Trp | Glu | Leu<br>205 | Lys | Glu | Asp |
| Tyr | Val<br>210 | Val | Val | Pro | Glu<br>215 | Asn | Ala | Val | Gly | Phe<br>220 | Thr | Ile | Tyr | Ala | Gln |
| Arg<br>225 | Thr | Ala | Gln | Ala | Gly<br>230 | Gln | Gly | Gly | Met | Arg<br>235 | Asn | Leu | Ser | Phe | Ser<br>240 |
| Glu | Val | Ser | Arg | Asn<br>245 | Gly | Gly | Ile | Ser | Lys<br>250 | Pro | Ala | Glu | Phe | Gly<br>255 | Val |
| Asn | Gly | Ile | Arg<br>260 | Val | Asn | Tyr | Ile | Cys<br>265 | Glu | Ser | Ala | Ser | Pro<br>270 | Pro | Asp |
| Ile | Met | Val<br>275 | Leu | Pro | Thr | Gln | Ala<br>280 | Ser | Ser | Lys | Thr | Gly<br>285 | Lys | Val | Phe |

Gly Gln Glu Phe Arg Glu Val
290                      295

(2) INFORMATION FOR SEQ ID NO:5:

(i) SEQUENCE CHARACTERISTICS:
        (A) LENGTH: 221 amino acids
        (B) TYPE: amino acid
        (D) TOPOLOGY: linear (ii) MOLECULE TYPE: protein (vi) ORIGINAL SOURCE:
        (A) ORGANISM: Bacteriophage T4

(vii) IMMEDIATE SOURCE:
        (B) CLONE: p36 amino acid (xi) SEQUENCE DESCRIPTION: SEQ ID NO:5:

```
Met Ala Asp Leu Lys Val Gly Ser Thr Thr Gly Gly Ser Val Ile Trp
 1               5                  10                  15
His Gln Gly Asn Phe Pro Leu Asn Pro Ala Gly Asp Asp Val Leu Tyr
             20                  25                  30
Lys Ser Phe Lys Ile Tyr Ser Glu Tyr Asn Lys Pro Gln Ala Ala Asp
         35                  40                  45
Asn Asp Phe Val Ser Lys Ala Asn Gly Gly Thr Tyr Ala Ser Lys Val
     50                  55                  60
Thr Phe Asn Ala Gly Ile Gln Val Pro Tyr Ala Pro Asn Ile Met Ser
 65                  70                  75                  80
Pro Cys Gly Ile Tyr Gly Gly Asn Gly Asp Gly Ala Thr Phe Asp Lys
                 85                  90                  95
Ala Asn Ile Asp Ile Val Ser Trp Tyr Gly Val Gly Phe Lys Ser Ser
             100                 105                 110
Phe Gly Ser Thr Gly Arg Thr Val Val Ile Asn Thr Arg Asn Gly Asp
         115                 120                 125
Ile Asn Thr Lys Gly Val Val Ser Ala Ala Gly Gln Val Arg Ser Gly
     130                 135                 140
Ala Ala Ala Pro Ile Ala Ala Asn Asp Leu Thr Arg Lys Asp Tyr Val
145                 150                 155                 160
Asp Gly Ala Ile Asn Thr Val Thr Ala Asn Ala Asn Ser Arg Val Leu
                 165                 170                 175
Arg Ser Gly Asp Thr Met Thr Gly Asn Leu Thr Ala Pro Asn Phe Phe
             180                 185                 190
Ser Gln Asn Pro Ala Ser Gln Pro Ser His Val Pro Arg Phe Asp Gln
         195                 200                 205
Ile Val Ile Lys Asp Ser Val Gln Asp Phe Gly Tyr Tyr
     210                 215                 220
```

(2) INFORMATION FOR SEQ ID NO:6:

(i) SEQUENCE CHARACTERISTICS:
        (A) LENGTH: 1026 amino acids
        (B) TYPE: amino acid
        (D) TOPOLOGY: linear (ii) MOLECULE TYPE: protein (vi) ORIGINAL SOURCE:
        (A) ORGANISM: Bacteriophage T4

(vii) IMMEDIATE SOURCE:
        (B) CLONE: p37 amino acid ( x i ) SEQUENCE DESCRIPTION: SEQ ID NO:6:

| Met | Ala | Thr | Leu | Lys | Gln | Ile | Gln | Phe | Lys | Arg | Ser | Lys | Ile | Ala | Gly |
| 1 | | | | 5 | | | | | 10 | | | | | 15 | |

| Thr | Arg | Pro | Ala | Ala | Ser | Val | Leu | Ala | Glu | Gly | Glu | Leu | Ala | Ile | Asn |
| | | | 20 | | | | 25 | | | | | 30 | | | |

| Leu | Lys | Asp | Arg | Thr | Ile | Phe | Thr | Lys | Asp | Ser | Gly | Asn | Ile | Ile |
| | | 35 | | | | | 40 | | | | | 45 | | |

| Asp | Leu | Gly | Phe | Ala | Lys | Gly | Gln | Val | Asp | Gly | Asn | Val | Thr | Ile |
| | 50 | | | | | 55 | | | | | 60 | | | |

| Asn | Gly | Leu | Leu | Arg | Leu | Asn | Gly | Asp | Tyr | Val | Gln | Thr | Gly | Gly | Met |
| 65 | | | | | 70 | | | | | 75 | | | | | 80 |

| Thr | Val | Asn | Gly | Pro | Ile | Gly | Ser | Thr | Asp | Gly | Val | Thr | Gly | Lys | Ile |
| | | | | 85 | | | | | 90 | | | | | 95 | |

| Phe | Arg | Ser | Thr | Gln | Gly | Ser | Phe | Tyr | Ala | Arg | Ala | Thr | Asn | Asp | Thr |
| | | | 100 | | | | | 105 | | | | | 110 | | |

| Ser | Asn | Ala | His | Leu | Trp | Phe | Glu | Asn | Ala | Asp | Gly | Thr | Glu | Arg | Gly |
| | | | 115 | | | | | 120 | | | | | 125 | | |

| Val | Ile | Tyr | Ala | Arg | Pro | Gln | Thr | Thr | Thr | Asp | Gly | Glu | Ile | Arg | Leu |
| | | 130 | | | | | 135 | | | | | 140 | | | |

| Arg | Val | Arg | Gln | Gly | Thr | Gly | Ser | Thr | Ala | Asn | Ser | Glu | Phe | Tyr | Phe |
| 145 | | | | | 150 | | | | | 155 | | | | | 160 |

| Arg | Ser | Ile | Asn | Gly | Gly | Glu | Phe | Gln | Ala | Asn | Arg | Ile | Leu | Ala | Ser |
| | | | | 165 | | | | | 170 | | | | | 175 | |

| Asp | Ser | Leu | Val | Thr | Lys | Arg | Ile | Ala | Val | Asp | Thr | Val | Ile | His | Asp |
| | | | 180 | | | | | 185 | | | | | 190 | | |

| Ala | Lys | Ala | Phe | Gly | Gln | Tyr | Asp | Ser | His | Ser | Leu | Val | Asn | Tyr | Val |
| | | 195 | | | | | 200 | | | | | 205 | | | |

| Tyr | Pro | Gly | Thr | Gly | Glu | Thr | Asn | Gly | Val | Asn | Tyr | Leu | Arg | Lys | Val |
| | | 210 | | | | | 215 | | | | | 220 | | | |

| Arg | Ala | Lys | Ser | Gly | Gly | Thr | Ile | Tyr | His | Glu | Ile | Val | Thr | Ala | Gln |
| 225 | | | | | 230 | | | | | 235 | | | | | 240 |

| Thr | Gly | Leu | Ala | Asp | Glu | Val | Ser | Trp | Trp | Ser | Gly | Asp | Thr | Pro | Val |
| | | | | 245 | | | | | 250 | | | | | 255 | |

| Phe | Lys | Leu | Tyr | Gly | Ile | Arg | Asp | Asp | Gly | Arg | Met | Ile | Ile | Arg | Asn |
| | | | 260 | | | | | 265 | | | | | 270 | | |

| Ser | Leu | Ala | Leu | Gly | Thr | Phe | Thr | Thr | Asn | Phe | Pro | Ser | Ser | Asp | Tyr |
| | | 275 | | | | | 280 | | | | | 285 | | | |

| Gly | Asn | Val | Gly | Val | Met | Gly | Asp | Lys | Tyr | Leu | Val | Leu | Gly | Asp | Thr |
| | 290 | | | | | 295 | | | | | 300 | | | | |

| Val | Thr | Gly | Leu | Ser | Tyr | Lys | Lys | Thr | Gly | Val | Phe | Asp | Leu | Val | Gly |
| 305 | | | | | 310 | | | | | 315 | | | | | 320 |

| Gly | Gly | Tyr | Ser | Val | Ala | Ser | Ile | Thr | Pro | Asp | Ser | Phe | Arg | Ser | Thr |
| | | | | 325 | | | | | 330 | | | | | 335 | |

| Arg | Lys | Gly | Ile | Phe | Gly | Arg | Ser | Glu | Asp | Gln | Gly | Ala | Thr | Trp | Ile |
| | | | 340 | | | | | 345 | | | | | 350 | | |

| Met | Pro | Gly | Thr | Asn | Ala | Ala | Leu | Leu | Ser | Val | Gln | Thr | Gln | Ala | Asp |
| | | | 355 | | | | | 360 | | | | | 365 | | |

| Asn | Asn | Asn | Ala | Gly | Asp | Gly | Gln | Thr | His | Ile | Gly | Tyr | Asn | Ala | Gly |
| | | 370 | | | | | 375 | | | | | 380 | | | |

| Gly | Lys | Met | Asn | His | Tyr | Phe | Arg | Gly | Thr | Gly | Gln | Met | Asn | Ile | Asn |
| 385 | | | | | 390 | | | | | 395 | | | | | 400 |

| Thr | Gln | Gln | Gly | Met | Glu | Ile | Asn | Pro | Gly | Ile | Leu | Lys | Leu | Val | Thr |
| | | | | 405 | | | | | 410 | | | | | 415 | |

```
Gly Ser Asn Asn Val Gln Phe Tyr Ala Asp Gly Thr Ile Ser Ser Ile
            420                 425                 430
Gln Pro Ile Lys Leu Asp Asn Glu Ile Phe Leu Thr Lys Ser Asn Asn
            435                 440                 445
Thr Ala Gly Leu Lys Phe Ala Pro Ser Gln Val Asp Gly Thr Arg
450                     455                 460
Thr Ile Gln Trp Asn Gly Gly Thr Arg Glu Gly Gln Asn Lys Asn Tyr
465                     470                 475                 480
Val Ile Ile Lys Ala Trp Gly Asn Ser Phe Asn Ala Thr Gly Asp Arg
            485                 490                 495
Ser Arg Glu Thr Val Phe Gln Val Ser Asp Ser Gln Gly Tyr Tyr Phe
            500                 505                 510
Tyr Ala His Arg Lys Ala Pro Thr Gly Asp Glu Thr Ile Gly Arg Ile
            515                 520                 525
Glu Ala Gln Phe Ala Gly Asp Val Tyr Ala Lys Gly Ile Ile Ala Asn
            530                 535                 540
Gly Asn Phe Arg Val Val Gly Ser Ser Ala Leu Ala Gly Asn Val Thr
545                     550                 555                 560
Met Ser Asn Gly Leu Phe Val Gln Gly Gly Ser Ser Ile Thr Gly Gln
            565                 570                 575
Val Lys Ile Gly Gly Thr Ala Asn Ala Leu Arg Ile Trp Asn Ala Glu
            580                 585                 590
Tyr Gly Ala Ile Phe Arg Arg Ser Glu Ser Asn Phe Tyr Ile Ile Pro
            595                 600                 605
Thr Asn Gln Asn Glu Gly Glu Ser Gly Asp Ile His Ser Ser Leu Arg
610                     615                 620
Pro Val Arg Ile Gly Leu Asn Asp Gly Met Val Gly Leu Gly Arg Asp
625                     630                 635                 640
Ser Phe Ile Val Asp Gln Asn Asn Ala Leu Thr Thr Ile Asn Ser Asn
                645                 650                 655
Ser Arg Ile Asn Ala Asn Phe Arg Met Gln Leu Gly Gln Ser Ala Tyr
            660                 665                 670
Ile Asp Ala Glu Cys Thr Asp Ala Val Arg Pro Ala Gly Ala Gly Ser
            675                 680                 685
Phe Ala Ser Gln Asn Asn Glu Asp Val Arg Ala Pro Phe Tyr Met Asn
690                     695                 700
Ile Asp Arg Thr Asp Ala Ser Ala Tyr Val Pro Ile Leu Lys Gln Arg
705                     710                 715                 720
Tyr Val Gln Gly Asn Gly Cys Tyr Ser Leu Gly Thr Leu Ile Asn Asn
                725                 730                 735
Gly Asn Phe Arg Val His Tyr His Gly Gly Asp Asn Gly Ser Thr
            740                 745                 750
Gly Pro Gln Thr Ala Asp Phe Gly Trp Glu Phe Ile Lys Asn Gly Asp
            755                 760                 765
Phe Ile Ser Pro Arg Asp Leu Ile Ala Gly Lys Val Arg Phe Asp Arg
            770                 775                 780
Thr Gly Asn Ile Thr Gly Gly Ser Gly Asn Phe Ala Asn Leu Asn Ser
785                     790                 795                 800
Thr Ile Glu Ser Leu Lys Thr Asp Ile Met Ser Ser Tyr Pro Ile Gly
                805                 810                 815
Ala Pro Ile Pro Trp Pro Ser Asp Ser Val Pro Ala Gly Phe Ala Leu
            820                 825                 830
Met Glu Gly Gln Thr Phe Asp Lys Ser Ala Tyr Pro Lys Leu Ala Val
            835                 840                 845
```

-continued

| Ala | Tyr 850 | Pro | Ser | Gly | Val | Ile 855 | Pro | Asp | Met | Arg | Gly 860 | Gln | Thr | Ile | Lys |
| Gly 865 | Lys | Pro | Ser | Gly | Arg 870 | Ala | Val | Leu | Ser | Ala 875 | Glu | Ala | Asp | Gly | Val 880 |
| Lys | Ala | His | Ser | His 885 | Ser | Ala | Ser | Ala | Ser 890 | Ser | Thr | Asp | Leu | Gly 895 | Thr |
| Lys | Thr | Thr | Ser 900 | Ser | Phe | Asp | Tyr | Gly 905 | Thr | Lys | Gly | Thr | Asn 910 | Ser | Thr |
| Gly | Gly | His 915 | Thr | His | Ser | Gly | Ser 920 | Gly | Ser | Thr | Ser | Thr 925 | Asn | Gly | Glu |
| His | Ser 930 | His | Tyr | Ile | Glu | Ala 935 | Trp | Asn | Gly | Thr | Gly 940 | Val | Gly | Gly | Asn |
| Lys 945 | Met | Ser | Ser | Tyr | Ala 950 | Ile | Ser | Tyr | Arg | Ala 955 | Gly | Gly | Ser | Asn | Thr 960 |
| Asn | Ala | Ala | Gly | Asn 965 | His | Ser | His | Thr | Phe 970 | Ser | Phe | Gly | Thr | Ser 975 | Ser |
| Ala | Gly | Asp | His 980 | Ser | His | Ser | Val | Gly 985 | Ile | Gly | Ala | His | Thr 990 | His | Thr |
| Val | Ala | Ile 995 | Gly | Ser | His | Gly | His 1000 | Thr | Ile | Thr | Val | Asn 1005 | Ser | Thr | Gly |
| Asn | Thr 1010 | Glu | Asn | Thr | Val | Lys 1015 | Asn | Ile | Ala | Phe | Asn 1020 | Tyr | Ile | Val | Arg |
| Leu 1025 | Ala | | | | | | | | | | | | | | |

MATERIALS FOR THE PRODUCTION OF NANOMETER STRUCTURES AND USE THEREOF

FIELD OF THE INVENTION

The present invention pertains to nanostructures, i.e. nanometer sized structures useful in the construction of microscopic and macroscopic structures. In particular, the present invention pertains to nanostructures based on bacteriophage T4 tail fiber proteins and variants thereof.

BACKGROUND TO THE INVENTION

While the strength of most metallic and ceramic based materials derives from the theoretical bonding strengths between their component molecules and crystallite surfaces, it is significantly limited by flaws in their crystal or glass-like structures. These flaws are usually inherent in the raw materials themselves or developed during fabrication and are often expanded due to exposure to environmental stresses.

The emerging field of nanotechnology has made the limitations of traditional materials more critical. The ability to design and produce very small structures (i.e. of nanometer dimensions) that can serve complex functions depends upon the use of appropriate materials that can be manipulated in predictable and reproducible ways, and that have the properties required for each novel application.

Biological systems serve as a paradigm for sophisticated nanostructures. Living cells fabricate proteins and combine them into structures that are perfectly formed and can resist damage in their normal environment. In some cases, intricate structures are created by a process of self-assembly, the instructions for which are built into the component polypeptides. Finally, proteins are subject to proofreading processes that insure a high degree of quality control.

Therefore, there is a need in the art for methods and compositions that exploit these unique features of proteins to form constituents of synthetic nanostructures. The need is to design materials whose properties can be tailored to suit the particular requirements of nanometer-scale technology. Moreover, since the subunits of most macrostructural materials, ceramics, metals, fibers, etc., are based on the bonding of nanostructural subunits, the fabrication of appropriate subunits without flaws and of exact dimensions and uniformity should improve the strength and consistency of the macrostructures because the surfaces are more regular and can interact more closely over an extended area than larger, more heterogeneous material.

SUMMARY OF THE INVENTION

In one aspect, the present invention provides isolated protein building blocks for nanostructures, comprising modified tail fiber proteins of bacteriophage T4. The gp34, 36, and 37 proteins are modified in various ways to form novel rod structures with different properties. Specific internal peptide sequences may be deleted without affecting their ability to form dimers and associate with their natural tail fiber partners. Alternatively, they may be modified so that they: interact only with other modified, and not native, tail fiber partners; exhibit thermolabile interactions with their partners; or contain additional functional groups that enable them to interact with heterologous binding moieties.

The present invention also encompasses fusion proteins that contain sequences from two or more different tail fiber proteins. The gp35 protein, which forms an angle joint, is modified so as to form average angles different from the natural average angle of 137°, and to exhibit thermolabile interactions with its partners.

In another aspect, the present invention provides nanostructures comprising native and modified tail fiber proteins of bacteriophage T4. The nanostructures may be one-dimensional rods, two-dimensional polygons or sheets, or three-dimensional open cages or closed solids.

BRIEF DESCRIPTION OF THE DRAWINGS

FIG. 2 shows a schematic representation of a unit rod.

FIGS. 3A–3D show schematic representations of: a one-dimensional multi-unit rod joined along the x axis (FIG. 3A); closed simple sheets (FIG. 3B); closed brickwork sheets (FIG. 3C); and open brickwork sheets (FIG. 3D).

FIG. 4 shows a schematic representation of two units used to construct porous solid structures (top and bottom), as well as the structures formed.

FIG. 5 shows a schematic representation of an angled structure having an angle of 120°.

FIG. 6 shows the DNA sequence SEQ.ID.NO.: 1 of genes 34, 35, 36, and 37 of bacteriophage T4.

FIG. 7 shows the amino acid sequences (shown in single-letter codes) of the gene products of genes 34 SEQ.ID.NO.: 2, ORFX SEQ.ID.NO: 3, 35 SEQ.ID.NO.: 4, 36 SEQ.ID.NO.: 5, and 37 SEQ.ID.NO.: 6 of bacteriophage T4. The amino acid sequences (bottom line of each pair) are aligned with the nucleotide sequences (top line of each pair.)

DETAILED DESCRIPTION OF THE INVENTION

Figure 1A:
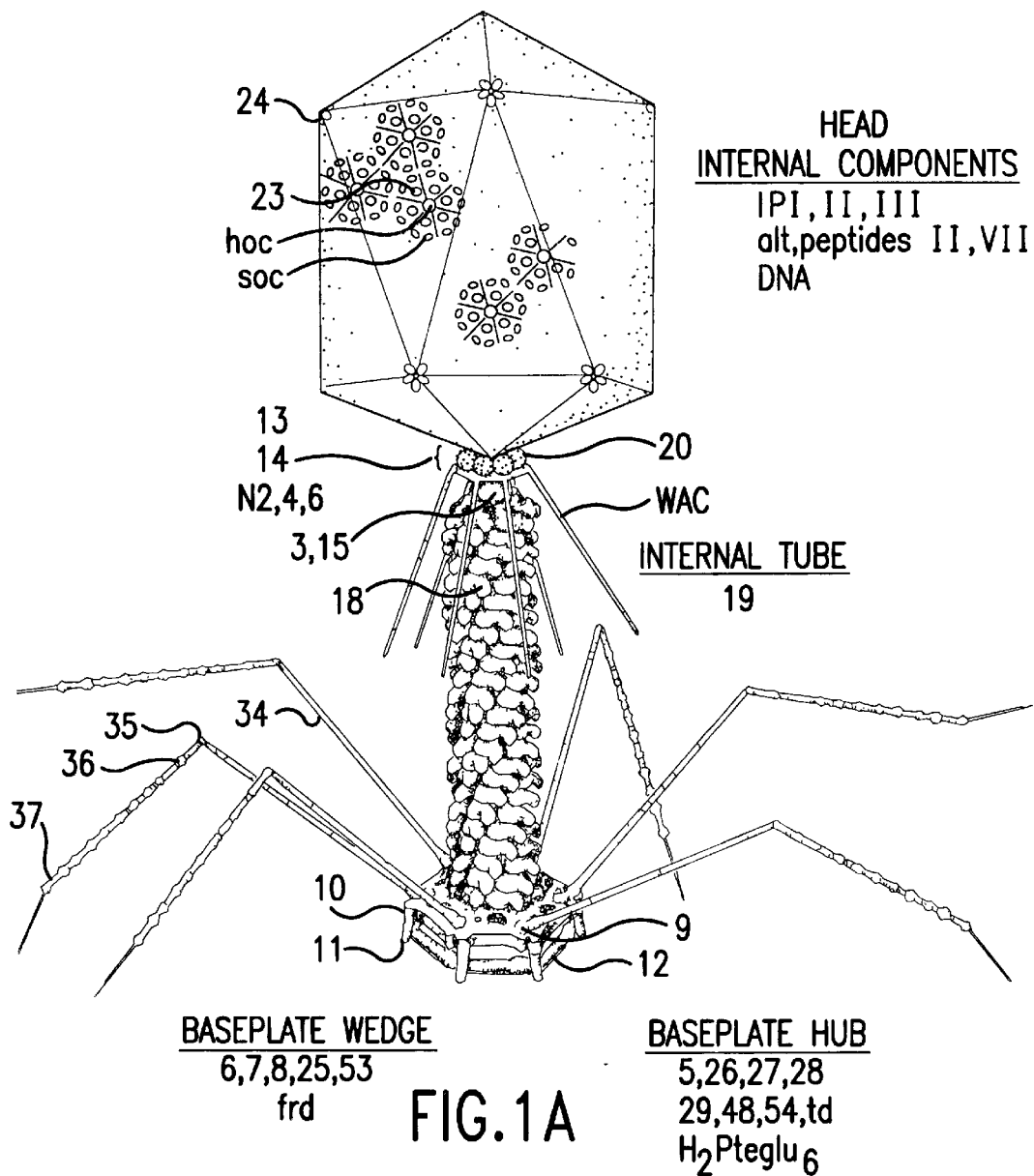
FIGS. 1A and 1B show a schematic representation of the T4 bacteriophage particle (FIG. 1A), and a schematic representation of the T4 bacteriophage tail fiber (FIG. 1B).

All patents, patent applications and literature references cited in the specification are hereby incorporated by reference in their entirety. In the case of inconsistencies, the present disclosure, including definitions, will prevail.

Definitions:

"Nanostructures" are defined herein as structures of different sizes and shapes that are assembled from nanometer-sized protein components.

"Chimers" are defined herein as chimeric proteins in which at least the amino- and carboxyterminal regions are derived from different original polypeptides, whether the original polpeptides are naturally occurring or have been modified by mutagenesis.

"Homodimers" are defined herein as assemblies of two substantially identical protein subunits that form a defined three-dimensional structure.

The designation "gp" denotes a monomeric polypeptide, while the designation "P" denotes homodimers as defined above.

An isolated polypeptide that "consists essentially of" a specified amino acid sequence is defined herein as a polypeptide having the specified sequence or a polypeptide that contains conservative substitutions within that sequence. Conservative substitutions, as those of ordinary skill in the art would understand, are ones in which an acidic residue is replaced by an acidic residue, a basic residue by a basic residue, or a hydrophobic residue by a hydrophobic residue. Also encompassed is a polypeptide that lacks one or more amino acids at either the amino terminus or carboxy terminus, up to a total of five at either terminus, when the absence of the particular residues has no discernable effect on the structure or the function of the polypeptide in practicing the present invention.

The present invention pertains to a new class of protein building blocks whose dimensions are measured in nanometers, which are useful in the construction of microscopic and macroscopic structures. Without wishing to be bound by theory, it is believed that the basic unit is a homodimer composed of two identical protein subunits having a cross-β configuration. These rod-shaped units can assemble with other rods using coupling devices that can be attached genetically or in vitro. The ends of one rod may attach to different ends of other rods or similar rods. Variations in the the length of the rods, in the angles of attachment, and in their flexibility characteristics permit differently-shaped structures to self-assemble in situ. In this manner the units can self-assemble into predetermined larger structures of one, two or three dimensions. The self-assembly can be staged to form structures of precise dimensions and uniform strength due to the flawless biological manufacture of the components. The rods can also be modified by genetic and chemical modifications to form predetermined specific attachment sites for other chemical entities, allowing the formation of complex structures.

An important aspect of the present invention is that the protein units can be designed so that they comprise rods of different lengths, and can be further modified to include features that alter their surface properties in predetermined ways and/or influence their ability to join with other identical or different units. Furthermore, the self-assembly capabilities can be expanded by producing chimeric proteins that combine the properties of two different members of this class. This design feature is achieved by manipulating the structure of the genes encoding these proteins.

As detailed below, the compositions and methods of the present invention take advantage of the properties of the natural proteins, i.e. the resulting structures are stiff, strong, stable in aqueous media, heat resistant, protease resistant, and can be rendered biodegradable. A large quantity of units can be fabricated easily in microorganisms. Furthermore, for ease of automation, large quantities of parts and subassemblies can be stored and used as needed.

The sequences of the protein subunits are based on the components of the tail fiber of the T4 bacteriophage of *E. coli*. It will be understood that the principles and techniques can be applied to the tail fibers of other T-even phages, or other related bacteriophages that have similar tail and/or fiber structures.

Figure 1B:
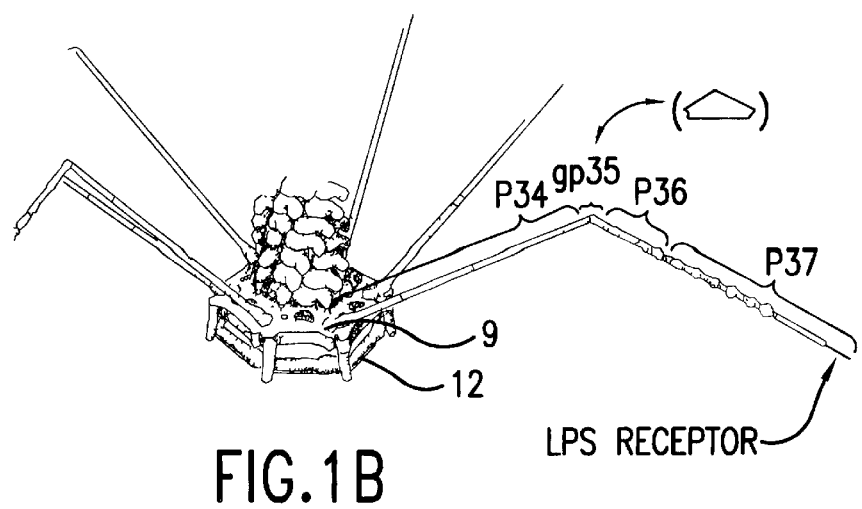

The structure of the T4 bacteriophage tail fiber (illustrated in FIG. 1) can be represented schematically as follows (N=amino terminus, C=carboxy terminus): N[P34]C–N[gp35]C–N[P36]C–N[P37]C. P34, P36, and P37 are all stiff, rod-shaped protein homodimers in which two identical β sheets, oriented in the same direction, are fused face-to-face by hydrophobic interactions between the sheets juxtaposed with a 180° rotational axis of symmetry through the long axis of the rod. gp35, by contrast, is a monomeric polypeptide that attaches specifically to the N-terminus of P36 and to the C-terminus of P34 and forms an angle joint between two rods.

During T4 infection of *E. coli*, two gp37 monomers dimerize to form a P37 homodimer; the process of dimerization is believed to initiate near the C-terminus of P37 and to require two *E. coli* chaperon proteins. (A variant gp37 with a temperature sensitive mutation near the C-terminus used in the present invention requires only one chaperon, gp57, for dimerization.) Once dimerized, the N-terminus of P37 initiates the dimerization of two gp36 monomers to a P36 rod. The joint between the C-terminus of P36 and the N-terminus of P37 is tight and stiff but noncovalent. The N-terminus of P36 then attaches to a gp35 monomer; this interaction stabilizes P36 and forms the elbow of the tail fiber. Finally, gp35 attaches to the C-terminus of P34 (which uses gp57 for dimerization). Thus, self assembly of the tail fiber is regulated by a predetermined order of interaction of specific subunits whereby structural maturation caused by formation of the first subassembly permits interaction with new (previously disallowed) subunits. This results in the production of a structure of exact specifications from a random mixture of the components.

In accordance with the present invention, the genes encoding these proteins may be modified so as to make rods of different lengths with different combinations of ends. The properties of the native proteins are particularly advantageous in this regard. First, the β-sheet is composed of antiparallel β-strands with β-bends at the left (L) and right (R) edges. Second, the amino acid side chains alternate up and down out of the plane of the sheet. The first property allows bends to be extended to form symmetric and specific attachment sites between the L and R surfaces, as well as to form attachment sites for other structures. In addition, the core sections of the β-sheet can be shortened or lengthened by genetic manipulations e.g. by splicing DNA regions encoding β-bends to form new bends that exclude intervening peptides, or by inserting segments of peptide in an analogous manner by splicing at bend angles. The second property allows amino acid side chains extending above and below the surface of the β-sheet to be modified by genetic substitution or chemical coupling. Importantly, all of the above modifications are achieved without compromising the structural integrity of the rod. It will be understood by one skilled in the art that these properties allow a great deal of flexibility in designing units that can assemble into a broad variety of structures, some of which are detailed below.

Structural Units

The rods of the present invention function like wooden 2×4 studs or steel beams for construction. In this case, the surfaces are exactly reproducible at the molecular level and thereby fitted for specific attachments to similar or different units rods at fixed joining sites. The surfaces are also modified to be more or less hydrophilic, including positively or negatively charged groups, and have protrusions built in for specific binding to other units or to an intermediate joint with two receptor sites. The surfaces of the rod and a schematic of the unit rod are illustrated in FIG. 2. The three dimensions of the rod are defined as: x, for the back (B) to front (F) dimension; y, for the down (D) to up (U) dimension; and z, for the left (L) to right (R) dimension.

One dimensional multi-unit rods can be most readily assembled from single unit rods joined along the x axis (FIG. 3A) but regular joining of subunits in either of the other two dimensions will also form a long structure, but with different cross sections than in the x dimension.

Figure 3C:
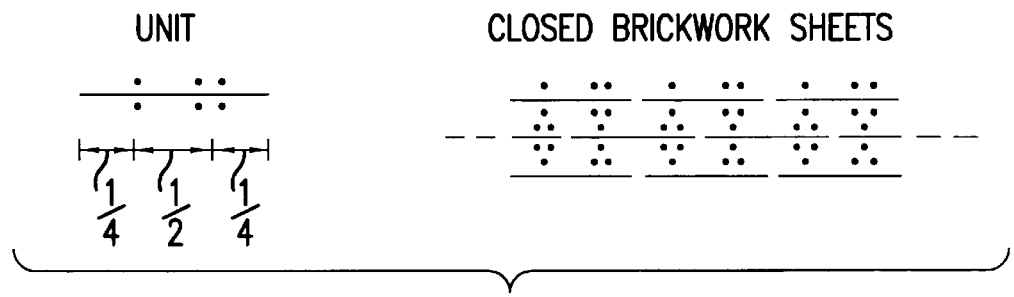
Figure 3D:
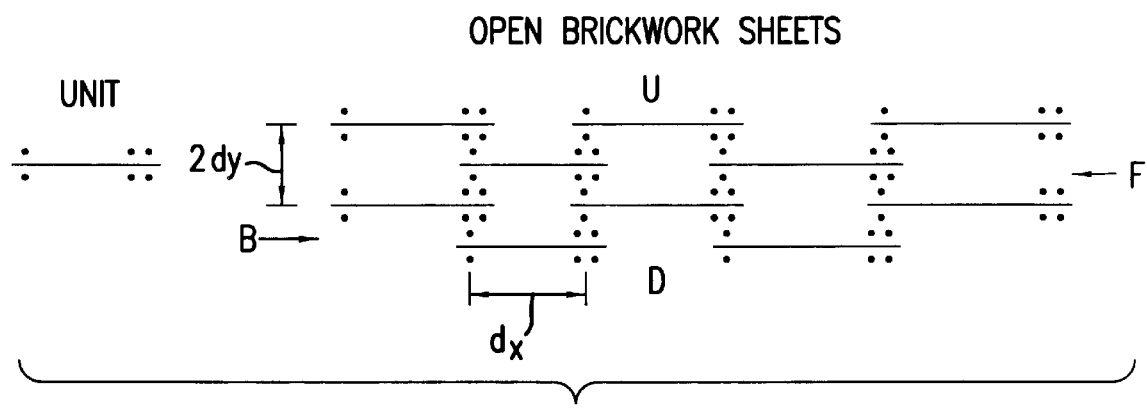

Two dimensional constructs are sheets formed by interaction of rods along any two axes. 1) Closed simple sheets are formed from surfaces which overlap exactly, along any two axes (FIG. 3B). 2) Closed brickwork sheets are formed from interaction between units that have exactly overlapping surfaces in one dimension and a special type of overlap in the other (FIG. 3C). In this case there must be two sets of complementary joints spaced with exactly ½ unit distance between them. If they are centered (i.e. each set ¼ from the end) then each joint will be in the center of the units above and below. If they are offset, then the joint will be offset as well. In this construction, the complementary interacting sites are schematized by "and". If the interacting sites are each symmetric, the alternating rows can interact with the rods in either direction. If they are not symmetric, and can only interact with interacting rows facing in the same or opposite direction, the sheet will be made of unidirectional rods or layers of rods in alternating directions. 3) Open brickwork sheets (or nets) result when the units are separated by more than one-half unit (FIG. 3D). The dimensions of the openings (or pores) depend upon the distance ($d_x$) separating the interacting sites and the distance ($d_y$) by which these sites separate the surfaces.

Three dimensional constructs require sterically compatible interactions between all three surfaces to form solids. 1) Closed solids can assemble from units that overlap exactly in all three dimensions (e.g. the exact overlapping of closed simple sheets). In an analogous manner, closed brickwork sheets can form closed solids by overlapping sheets exactly or displaced to bring the brickwork into the third dimension. This requires an appropriate set of joints on all three faces of the unit. 2) Porous solids are made by joining open brickwork sheets in various ways. For example, if the units overlap exactly in the third dimension, a solid is formed with the array of holes of exact dimensions running perpendicular to the plane of the paper. If instead, a material is needed with closed spaces, with layers of width $d_z$ (i.e. in the U→D dimension), a simple closed sheet is layered on the open brickwork sheet to close the openings. If the overlap of the open brickwork sheet is e.g. ¼ unit, then a rod of length ¾ units is used to make the sheet. Joints are then needed in the z dimension. The two units used to polymerize these alternate layers, and the layers themselves, are schematized in FIG. 4.

All of the above structures are composed of simple linear rods. A second unit, the angle unit, expands the type and dimensionality of possible structures. The angle unit connects two rods at angles different from 180°, akin to an angle iron. The average angle and its degree of rigidity are built into this connector structure. For example, the structure shown in FIG. 5 has an angle of 120° and different specific joining sites at a and at b. The following are examples of structures that are formed utilizing angle joints:

1) Open brickwork sheets are expanded and strengthened in the direction normal to the rod direction by adding angles perpendicular to the sheet. In this case, a three dimensional network forms. Attachment of 90° angles to the ends of the rods makes an angle almost in the plane of the sheet, allowing new rods added to those angles (which must have some play out of the plane of the original sheet to attach in the first place) to form a new sheet, almost parallel, with an orientation normal to its upper or lower neighbor.

2) Hexagons are made from a mixture of rods and angle joints that form 120° angles. In this case, there are two exclusive sets of joints. Each set is made up of one of the two ends of the rod and one of the two complementary sites on the angle. This is a linear structure in the sense that the hexagon has a direction (either clockwise or counterclockwise). It can be made into a two dimensional open net (i.e. a two dimensional honeycomb) by joining the sides of the hexagons. It can form hexagonal tubes by joining the top of the hexagon below to the bottom face of the hexagon above. If the tubes also join by their sides, they will form an open three dimensional multiple hexagonal tube.

3) Helical hexagonal tubes are made analogously to hexagons but the sixth unit is not joined to the first to close the hexagon. Instead, the end is displaced from the plane of the hexagon and the seventh and further units are added to form a hexagonal tube which can be a spring if there is little or no adhesive force between the units of the helix, or a stiff rod if there is such a force to maintain the close proximity of apposing units.

It will be apparent to one skilled in the art that the compositions and methods of the present invention also encompass other polygonal structures such as octagons, as well as open solids such as tetrahedrons and icosahedrons formed from triangles and boxes formed from squares and rectangles. The range of structures is limited only by the types of angle units and the substituents that can be engineered on the different axes of the rod units. For example, other naturally occurring angles are found in the fibers of bacteriophage T7, which has a 90° angle (Steven et al., J.Mol.Biol. 200: 352–365, 1988).

Design and Production of the Rod Proteins

The protein subunits that are used to construct the nanostructures of the present invention are based on the four polypeptides that comprise the tail fibers of bacteriophage T4, i.e. gp34, gp35, gp36 and gp37. The genes encoding these proteins have been cloned, and their DNA and protein sequences have been determined (for gene 36 and 37 see Oliver et al. J.Mol.Biol. 153: 545–568, 1981). The DNA and amino acid sequences of genes 34, 35, 36 and 37 are set forth in FIGS. 6 and 7 below.

Gp34, gp35, gp36, and gp37 are produced naturally following infection of E. coli cells by intact T4 phage particles. Following synthesis in the cytoplasm of the bacterial cell, the gp34, 36, and 37 monomers form homodimers, which are competent for assembly into maturing phage particles. Thus, E. coli serves as an efficient and convenient factory for synthesis and dimerization of the protein subunits described herein below.

In practicing the present invention, the genes encoding the proteins of interest (native, modified, or recombined) are incorporated into DNA expression vectors that are well known in the art. These circular plasmids typically contain selectable marker genes (usually conferring antibiotic resistance to transformed bacteria), sequences that allow replication of the plasmid to high copy number in E. coli, and a multiple cloning site immediately downstream of an inducible promoter and ribosome binding site. Examples of commercially available vectors suitable for use in the present invention include the pET system (Novagen, Inc., Mdison, Wis.) and Superlinker vectors pSE280 and pSE380 (Invitrogen, San Diego, Calif.).

The strategy is to 1) construct the gene of interest and clone it into the multiple cloning site; 2) transform E. coli cells with the recombinant plasmid; 3) induce the expression of the cloned gene; 4) test for synthesis of the protein product; and, finally, 5) test for the formation of functional homodimers. In some cases, additional genes are also cloned into the same plasmid, when their function is required for dimerization of the protein of interest. For example, when wild-type or modified versions of gp37 are expressed, the bacterial chaperon gene 57 is also included; when wild-type or modified gp36 is expressed, the wild-type version or a modified version of the gp37 gene is included. The modified gp37 should have the capacity to dimerize and contain an N-terminus that can chaperon the dimerization of gp36. This method allows the formation of monomeric gene products and, in some cases, maturation of monomers to homodimeric rods in the absence of other phage-induced proteins normally present in a T4-infected cell.

Steps 1–4 of the above-defined strategy are achieved by methods that are well known in the art of recombinant DNA technology and protein expression in bacteria. For example, in step 1, restriction enzyme cleavage at multiple sites, followed by ligation of fragments, is used to construct deletions in the internal rod segment of gp34, 36, and 37 (see Example 1 below). Alternatively, a single or multiple restriction enzyme cleavage, followed by exonuclease digestion (EXO-SIZE, New England Biolabs, Beverly, Mass.), is used to delete DNA sequences in one or both directions from the initial cleavage site; when combined with a subsequent ligation step, this procedure produces a nested set of deletions of increasing sizes. Similarly, standard methods are used to recombine DNA segments from two different tail fiber genes, to produce chimeric genes encoding fusion proteins (called "chimers" in this description). In general, this last method is used to provide alternate N- or C-termini and thus create novel combinations of ends that enable new patterns of joining of different rod segments. A representative of this type of chimer, a fusion of P37-P36, is described in Example 2. The preferred hosts for production of these proteins (Step 2) is $E.$ $coli$ strain BL21(DE3) and BL21 (DE3/pLysS) (available commercially from Novagen, Madison, Wis.), although other compatible recA strains, such as HMS174(DE3) and HMS174(DE3/pLysS) can be used. Transformation with the recombinant plasmid (Step 2) is accomplished by standard methods (Sambrook, J., *Molecular Cloning,* Cold Spring Harbor Laboratories, Cold Spring Harbor, N.Y.; this is also the source for standard recombinant DNA methods used in this invention.) Transformed bacteria are selected by virtue of their resistance to antibiotics e.g. ampicillin or kanamycin.

The method by which expression of the cloned tail fiber genes is induced (Step 3) depends upon the particular promoter used. A preferred promoter is plac (with a $laci^q$ on the vector to reduce background expression), which can be regulated by the addition of isopropylthiogalactoside (IPTG). A second preferred promoter is pT7φ10, which is specific to T7 RNA polymerase and is not recognized by $E.$ $coli$ RNA polymerase. T7 RNA polymerase, which is resistant to rifamycin, is encoded on the defective lambda DE lysogen in the $E.$ $coli$ BL21 chromosome. T7 polymerase in BL21(DE3) is super-repressed by the $laci^q$ gene in the plasmid and is induced and regulated by IPTG.

Typically, a culture of transformed bacteria is incubated with the inducer for a period of hours, during which the synthesis of the protein of interest is monitored. In the present instance, extracts of the bacterial cells are prepared, and the T4 tail fiber proteins are detected, for example, by SDS-polyacrylamide gel electrophoresis.

Once the modified protein is detected in bacterial extracts, it is necessary to ascertain whether or not it forms appropriate homodimers (Step 4). This is accomplished initially by testing whether the protein is recognized by an antiserum specific to the mature dimerized form of the protein.

Tail fiber-specific antisera are prepared as described (Edgar, R. S. and Lielausis, I., *Genetics* 52: 1187, 1965; Ward et al, *J. Mol. Biol.* 54: 15, 1970). Briefly, whole T4 phage are used as an immunogen; the resulting antiserum is then adsorbed with tail-less phage particles, thus removing all antibodies except those directed against the tail fiber proteins. In a subsequent step, different aliquots of the antiserum are adsorbed individually with extracts that each lack a particular tail fiber protein. For example, if an extract containing only tail fiber components P34, gp35, and gp36 (derived from a cell infected with a mutant T4 lacking a functional gp37 gene) is used for absorption, the resulting antiserum will recognize only mature P37 and dimerized P36-P37. A similar approach may be used to prepare individual antisera that recognize only mature (i.e. homodimerized) P34 and P36 by adsorbing with extracts containing distal half tail fibers or P34, gp35 and P37, respectively. An alternative is to raise antibody against purified tail fiber halves, e.g. P34 and gp35-P36-P37. Anti gp35-P36-P37 can then be adsorbed with P36-P37 to produce anti-gp35, and anti-P36 can be produced by adsorption with P37 and gp35. Anti-P37, anti-gp35, and anti-P34 can also be produced directly by using purified P37, gp35, and P34 as immunogens. Another approach is to raise specific monoclonal antibodies against the different tail fiber components or segments thereof.

Specific antibodies to subunits or tail parts are used in any of the following ways to detect appropriately homodimerized tail fiber proteins: 1) Bacterial colonies are screened for those expressing mature tail fiber proteins by directly transferring the colonies, or, alternatively, samples of lysed or unlysed cultures, to nitrocellulose filters, lysing the bacterial cells on the filter if necessary, and incubating with specific antibodies. Formation of immune complexes is then detected by methods widely used in the art (e.g. secondary antibody conjugated to a chromogenic enzyme or radiolabelled Staphylococcal Protein A.). This method is particularly useful to screen large numbers of colonies e.g. those produced by EXO-SIZE deletion as described above. 2) Bacterial cells expressing the protein of interest are first metabolically labelled with $^{35}$S-methionine, followed by preparation of extracts and incubation with the antiserum. The immune complexes are then recovered by incubation with immobilized Protein A followed by centrifugation, after which they may be resolved by SDS-polyacrylamide gel electrophoresis.

An alternative competitive assay for testing whether internally deleted tail fiber proteins that do not permit phage infection nonetheless retain the ability to dimerize and associate with their appropriate partners utilizes an in vitro complementation system. 1) A bacterial extract containing the modified protein of interest, as described above, is mixed with a second extract prepared from cells infected with a T4 phage that is mutant in the gene of interest. 2) After several hours of incubation, a third extract is added that contains the wild-type version of the protein being tested, and incubation is continued for several additional hours. 3) Finally, the extract is titered for infectious phage particles by infecting $E.$ $coli$ and quantifying the phage plaques that result. A modified tail fiber protein that is correctly dimerized and able to join with its partners is incorporated into tail fibers in a non-functional manner in Step 1, thereby preventing the incorporation of the wild-type version of the protein in Step 2; the result is a reduction in the titer of the resulting phage sample. By contrast, if the modified protein is unable to dimerize and thus form proper N- and/or C-termini, it will not be incorporated into phage particles in Step 1, and thus will not compete with assembly of intact phage particles in Step 2; the phage titer should thus be equivalent to that observed when no modified protein is added in Step 1 (a negative control.)

The above-described methods are used, alone and in combination, in the design and production of different types of modified tail fiber proteins. For example, a preliminary screen of a large number of bacterial colonies for those expressing a properly dimerized protein will identify positive colonies, which can then be individually tested by in vitro complementation.

Non-limiting examples of novel proteins that are encompassed by the present invention include:

1) Internally deleted gp34, 36, and 37 polypeptides (See Example 1 below);

2) A C-terminally truncated gp36 fused to the N-terminus of N-terminally truncated gp37;

3) A fusion between gp36 and gp37 in which gp37 is N-terminal to gp36 (i.e. in reverse of the natural order), termed herein "gp37-36 chimer" (See Example 2 below);

4) A variant of gp36 in which the C-terminus is mutated such that it lacks the capability to interact with (and dimerize in response to) the N-terminus of wild-type P37, termed herein "gp36*";

5) A variant of gp37 in which the N-terminus is mutated such that it lacks the capability to interact with the C-terminus of wild-type gp36, termed herein "*P37";

6) Variants of gp36* and *P37 that can interact with each other, but not with gp36 or P37.

7) A variant "P37-36 chimer" in which the gp36 moiety is derived from the variant as in 4), i.e. "P37-36*". (For 4)–7), See Example 3 below.)

8) A variant "P37-36 chimer" in which the gp37 moiety is derived from the variant as in 5) above, i.e. "*P37-36".

9) A variant P37-36 chimer, *P37-P36*, in which the gp36 and gp37 moieties are derived from the variants in 6).

10) A fusion between gp36 and gp34 in which gp36 sequences are placed N-terminal to gp34, the dimer of which is termed herein "P36-34 chimer";

11) Variants of gp35 that form average angles different from 137° C. (the native angle) e.g. less than about 125° or more than about 145°, and/or exhibit more or less flexibility than the native polypeptide;

12) Variants of gp34, 35, 36 and 37 that exhibit thermolabile interactions or other variant specific interactions with their cognate partners; and 13) Variants of gp37 in which the C-terminal domain of the polypeptide is modified to include sequences that confer specific binding properties on the entire molecule, e.g. sequences derived from avidin that recognize biotin, sequences derived from immunoglobulin heavy chain that recognize Staphylococcal A protein, sequences derived from the Fab portion of the heavy chain of monoclonal antibodies to which their respective Fab light chain counterparts could attach and form an antigen-binding site, immunoactive sequences that recognize specific antibodies, or sequences that bind specific metal ions. These ligands may be immobilized to facilitate purification and/or assembly.

Assembly of Individual Rod Components into Nanostructures

Expression of the proteins of the present invention in E. coli as described above results in the synthesis of large quantities of protein, and allows the simultaneous expression and assembly of different components in the same cells. The methods for scale-up of recombinant protein production are straightforward and widely known in the art, and many standard protocols can be used to recover native and modified tail fiber proteins from a bacterial culture.

P34, P36-P37, P37, and chimers derived from them are purified from E. coli cultures as mature dimers. Gp35 and variants thereof are purified as monomers. Purification is achieved by the following procedures or combinations thereof, using standard methods: 1) Sequential chromatography on molecular sieve, ion-exchange, and hydrophobic matrices; 2) preparative ultracentrifugation; and 3) affinity chromatography, using as the immobilized ligand specific antibodies or other specific binding moieties. For example, the C-terminal domain of P37 binds to the lipopolysaccharide of E. coli B. Other T4-like phages have P37 analogues that bind other cell surface components such as OmpF or TSX protein. Alternatively, if the proteins have been engineered to include heterologous domains that act as ligands or binding sites, the cognate partner is immobilized on a solid matrix and used in affinity purification.

Alternatively, several components are co-expressed in the same bacterial cells, and sub-assemblies of larger nanostructures are purified subsequent to limited in vivo assembly, using the methods enumerated above.

The purified components are then combined in vitro under conditions where assembly of the desired nanostructure occurs at temperatures between about 4° C. and about 37° C., and at pHs between about 5 and about 9. For a given nanostructure, optimal conditions for assembly (i.e. type and concentration of salts and metal ions) are easily determined by routine experimentation, such as by changing each variable individually and monitoring formation of the appropriate products.

Alternatively, one or more crude bacterial extracts may be prepared, mixed, and assembly reactions allowed to proceed prior to purification.

In some cases, one or more purified components assemble spontaneously into the desired structure, without the necessity for initiators. In other cases, an initiator is required to nucleate the polymerization of rods or sheets. This offers the advantage of localizing the assembly process (i.e. if the initiator is immobilized or otherwise localized) and of regulating the dimensions of the final structure. For example, rod components that contain a functional P36 C-terminus require a functional P37 N-terminus to initiate rod formation stoichiometrically; thus, altering the relative amount of initiator and rod component will influence the average length of rod polymer. If the ratio is n, the average rod will be approximately (P37-36)n—N-terminus P37-P37 C-terminus.

In still other cases, the final nanostructure is composed of two or more components that cannot self-assemble individually but only in combination with each other. In this situation, alternating cycles of assembly can be staged to produce final products of precisely defined structure (see Example 6B below.)

When an immobilized initiator is used, it may be desirable to remove the polymerized unit from the matrix after staged assembly. For this purpose specialized initiators are engineered so that the interaction with the first rod component is rendered reversibly thermolabile (see Example 5 below). In this way, the polymer can be easily separated from the matrix-bound initiator, thereby permitting: 1) easy preparation of stock solutions of uniform parts or subassemblies, and 2) re-use of the matrix-bound initiator for multiple cycles of polymer initiation, growth, and release.

Applications

The uses of the nanostructures of the present invention are manifold and include applications that require highly regular, well-defined arrays of fibers, cages, or solids, which may include specific attachment sites that allow them to associate with other materials.

In one embodiment, a three-dimensional honeycomb array is used as a molecular filter, providing regular vertical pores of precise diameter for selective separation of particles by size. Such filters can be used for sterilization of solutions (i.e. to remove microorganisms or virusus), or as a series of molecular-weight cut-off filters. In this case, the protein components of the pores may be modified so as to provide specific surface properties (i.e. hydrophilicity or hydrophobicity, ability to bind specific ligands, etc.). Among the advantages of ths type of filtration device is the uniformity and linearity of pores and the high pore to matrix ratio.

In another embodiment, long one-dimensional fibers are incorporated, for example, into paper or cement during manufacture to provide added wet and dry tensile strength.

In still another embodiment, different nanostructure arrays are impregnated into paper and fabric as anti-counterfeiting markers. In this case, a simple color-linked antibody reaction (such as those commercially available in kits) is used to verify the origin of the material. Alternatively, such nanostructure arrays could bind dyes or other substances, either before or after incorporation to color the paper or fabrics or modify their appearance or properties in other ways.

The following examples are intended to illustrate the present invention without limiting its scope.

In the examples below, all restriction enzymes, nucleases, ligases, etc. are commercially available from numerous commercial sources, such as New England Biolabs (NEB), Beverly, Mass.; Life Technologies (GIBCO-BRL), Gaithersburg, Md.; and Boehringer Mannheim Corp. (BMC), Indianapolis, Ind.

EXAMPLE 1

Design, Construction and Expression of Internally Deleted P37

The gene encoding gp37 contains two sites for the restriction enzyme Bgl II, the first cleavage occurring after nucleotide 293 and the second after nucleotide 1486 (the nucleotides are numbered from the initiator methionine codon ATG.) Thus, digestion of a DNA fragment encoding gp37 with Bgl II, excision of the intervening fragment (nucleotides 294–1485) and re-ligation of the 5' and 3' fragments results in the formation of an internally deleted gp37, designated ΔP37, in which arginine-98 is joined with serine-497.

The restriction digestion reaction mix contains:

| | |
|---|---|
| gp37 plasmid DNA (1 μg/μl) | 2 μl |
| NEB buffer #2 (10X) | 1 μl |
| H$_2$O | 6 μl |
| Bgl II (10 U/μl) | 1 μl |

The gp37 plasmid signifies a pT7-5 plasmid into which gene 37 has been inserted in the multiple cloning site, downstream of a good ribosome binding site and of gene 57 to chaperon the dimerization. The reaction is incubated for 1 h at 37° C. Then, 89 μl of T4 DNA ligase buffer and 1 μl of T4 DNA ligase are added, and the reaction is continued at 16° C. for 4 hours. 2 μl of the Stu I restriction enzyme are then added, and incubation continued at 37° C. for 1 h. (The Stu I restriction enzyme digests residual plasmids that were not cut by Bgl II in the first step, reducing their transformability by about 100-fold.)

The reaction mixture is then transformed into E. coli strain BL21, obtained from Novagen, using standard procedures. The transformation mixture is plated onto nutrient agar containing 100 μg/ml ampicillin, and the plates are incubated overnight at 37° C.

Colonies that appear after overnight incubation are picked, and plasmid DNA is extracted and digested with Bgl II as above. The restriction digests are resolved on 1% agarose gels. A successful deletion is evidenced by the appearance after gel electrophoresis of a new DNA fragment of 4.2 kbp, representing the undeleted part of gene 37 which is still attached to the plasmid and which re-formed a BglII site by ligation. The 1.2 kbp DNA fragment bounded by BglII sites in the original gene is no longer in the plasmid and so is missing from the gel.

Plasmids selected for the predicted deletion as above are transformed into E. coli strain BL21(DE3). Transformants are grown at 30° C. until the density ($A_{600}$) of the culture reaches 0.6. IPTG is then added to a final concentration of 0.4 mM and incubation is continued at 30° C. for 2 h, after which the cultures are chilled on ice. 20 μl of the culture is then removed and added to 20 μl of a two-fold concentrated "cracking buffer" containing 1% sodium dodecyl sulfate, glycerol, and tracking dye. 15 μl of this solution are loaded onto a 10% polyacrymide gel; a second aliquot of 15 μl is first incubated in a boiling water bath for 3 min and then loaded on the same gel. After electrophoresis, the gel is fixed and stained. Expression of the deleted gp37 is evidenced by the appearance of a protein species migrating at an apparent molecular mass of 65–70,000 daltons in the boiled sample. The extent of dimerization is suggested by the intensity of higher-molecular mass species in the unboiled sample and/or by the disappearance of the 65–70,000 dalton protein band.

The ability of the deleted polypeptide to dimerize appropriately is directly evaluated by testing its ability to be recognized by an anti-P37 antiserum that reacts only with mature P37 dimers, using a standard protein immunoblotting procedure.

An alternative assay for functional dimerization of the deleted polypeptide is its ability to form a P36 dimer on its N-terminus. This is detected by specific anti-P36 antiserum, or by the ability of the deleted P37 (also referred to as ΔP37) to inhibit an in vitro gp36 dimerization assay by sequestering much of the gp36 with the deleted P37.

EXAMPLE 2

Design, Construction and Expression of a gp37-36 Chimer

The starting plasmid for this construction is one in which the gene encoding gp37 is cloned immediately upstream (i.e. 5') of the gene encoding gp36. The plasmid is digested with Hae III, which deletes the entire 3' region of gp37 DNA downstream of nucleotide 724 to the 3' terminus, and also removes the 5' end of gp36 DNA from the 5' terminus to nucleotide 349. The reaction mixture is identical to that described in Example 1, except that a different plasmid DNA is used, and the enzyme is HaeIII. Ligation using T4 DNA ligase, bacterial transformation, and restriction analysis are also performed as in Example 1. In this case, excision of the central portion of the gene 37-36 insert and religation reveals a novel insert of 346 in-frame codons, which is cut only once by HaeIII (after nucleotide 725). The resulting construct is then expressed in E. coli BL21(DE3) as described in Example 1.

Successful expression of the gp37-36 chimer is evidenced by the appearance of a protein product of about 35,000 daltons. This protein will have the first 242 N-terminal amino acids of gp37 fused to the final 104 C-terminal amino acids of gp36 (numbered 118–221.) The utility of this chimer depends upon its ability to dimerize and attach end-to-end. That is, two carboxy termini of said polypeptide will have the capability of interacting with the amino terminus of the P37 protein dimer of bacteriophage T4 and to form an attached dimer, and the amino terminus of the dimer of said polypeptide will have the capability of interacting with another pair of said chimer polypeptides. This property can be tested by assaying whether introduction of ΔP37 initiates dimerization and polymerization. Alternatively, polyclonal antibodies specific to P36 dimer may be used to detect P36 subsequent to initiation of dimerization by ΔP37.

EXAMPLE 3

Mutation of the GP37-36 Chimer to Produce Complementary Suppressors

The goal of this construction is to produce two variants of a dimerizable P37-36 chimer: One in which the N-terminus of the polypeptide is mutated (A, designated *P37-36) and one in which the C-terminus of the polypeptide is mutated (B, designated P37-36*). The requirement is that the mutated *P37 N-terminus cannot form a joint with the wild-type P36 C-terminus, but only with the mutated *P36 N-terminus. The rationale is that A and B each cannot polymerize independently (as the parent P37-36 protein can), but can only associate with each other sequentially (i.e. P37-36*+*P37-36→P37-36*-*P37-36).

A second construct, *p37-P36*, is formed by recombining *P37-36 and P37-36* in vitro. When the monomers *gp37-36* and gp37-36 are mixed in the presence of P37 initiator, gp37-36 would dimerize and polymerize to (P37-36)n; similarly, *P37 would only catalyze the polymerization of *gp37-36* to (*P37-36*)n. In this case, the two chimers could be of different size and different primary sequence with different potential side-group interactions, and could initiate attachment at different surfaces depending on the attachment specificity of P37.

The starting bacterial strain is a sup$^o$ strain of *E. coli* (which lacks the ability to suppress amber mutations). When this strain is infected with a mutant T4 bacteriophage containing amber mutations in genes 35, 36, and 37, phage replication is incomplete, since the tail fiber proteins cannot be synthesized. When this strain is first transformed with a plasmid that directs the expression of the wild type gp35, gp36 and gp37 genes and induced with IPTG, and subsequently infected with mutant phage, infectious phage particles are produced; this is evidenced by the appearance of "nibbled" colonies. Nibbled colonies do not appear round, with smooth edges, but rather have sectors missing. This is caused by attack of a microcolony by a single phage, which replicates and prevents the growth of the bacteria in the missing sector.

For the purposes of this construction, the 3'-terminal region of gene 36 (corresponding to the C-terminal region of gp36) is mutagenized with randomly doped oligonucleotides. Randomly doped oligonucleotides are prepared during chemical synthesis of oligonucleotides, by adding a trace amount (up to a few percent) of the other three nucleotides at a given position, so that the resulting oligonucleotide mix has a small percentage of incorrect nucleotides at that position. Incorporation of such oligonucleotides into the plasmid will result in random mutations (Hutchison et al., Methods.Enzymol. 202: 356, 1991).

The mutagenized population of plasmids (containing, however, unmodified genes 36 and 37), is then transformed into the sup$^o$ bacteria, followed by infection with the mutant T4 phage as above. In this case, the appearance of non- "nibbled" colonies indicates that the mutated gp36 C-termini can no longer interact with wild type P37 to form functional tail fibers. The putative gp36* phenotypes found in such non-nibbled colonies are checked for lack of dimeric N-termini by appropriate immunospecificity as outlined above, and positive colonies are used as source of plasmid for the next step.

Several of these mutated plasmids are recovered and subjected to a second round of mutagenesis, this time using doped oligonucleotides that introduce random mutations into the N-terminal region of gp37 present on the same plasmid. Again, the (now doubly) mutagenized plasmids are transformed into the sup$^o$ strain of *E. coli* and transformants are infected with the mutant T4 phage. At this stage, bacterial plates are screened for the re-appearance of "nibbled" colonies. A nibbled colony at this stage indicates that the phage has replicated by virtue of suppression of the non-functional gp36* mutation(s) by the *P37 mutation. In other words, such colonies must contain novel *P37 polypeptides that have now acquired the ability to interact with the P36* proteins encoded on the same plasmid.

The *P37-36 and P37-36* paired suppressor chimers (A and B as above) are then constructed in the same manner as described in Example 2. In this case, however, *P37 is used in place of wild type P37 and P36* is used in place of wild type P36. A *P37-36* chimer can now be made by restriction of *P37-36 and P37-36* and religation in the recombined order. The *P37-36* can be mixed with the P37-36 chimer, and the polymerization of each can be accomplished independently in the presence of the other. This is useful when the rod-likecentral portion of these chimers have been modified in different ways.

EXAMPLE 4

Design, Construction and Expression of a gp36-34 Chimer

The starting plasmid for this construction is one in which the vector containing gene 57 and the gene encoding gp36 is cloned immediately upstream (i.e. 5') of the gene encoding gp34. The plasmid is digested with NdeI, which cuts after bp 219 of gene 36 and after bp 2594 of gene 34, thereby deleting the final 148 C-terminal codons from the pg36 moiety and the first 865 N-terminal codons from the gp34 moiety. The reaction mixture is identical to that described in Example 1, except that a different plasmid DNA is used, and the enzyme used is NdeI (NEB). Ligation using T4 DNA ligase, bacterial transformation, and restriction analysis are also performed as in Example 1. This results in a new hybrid gene encoding a protein of 497 amino acids (73 N-terminal amino acids of gp36 and 424 C-terminal amino acids of gp34, numbered 866–1289.)

As an alternative, the starting plasmid is cut with SphI at bp 648 in gene 34, and the Exo-Size Deletion Kit (NEB) is used to create deletions as described above.

The resulting construct is then expressed in *E. coli* BL21 (DE3) as described in Example 1. Successful expression of the gp36-34 chimer is evidenced by the appearance of a protein product of about 55,000 daltons. Preferably, the amino termini of the polypeptide homodimer have the capability of interacting with the gp35 protein, and the carboxy termini have the capability of interacting with gp35. Successful formation of the dimer can be detected by reaction with anti-P36 antibodies or by attachment of gp35.

EXAMPLE 5

Isolation of Thermolabile Proteins for Self-Assembly

Thermolabile structures can be utilized in nanostructures for: a) initiation of chimer polymerization (e.g. gp37-36) at low temperature and subsequent inactivation of and separation from the initiator at high temperature; b) initiation of angle formation between P36 and gp35 (e.g. variants of gp35 that have thermolabile attachment sites for P36 N-termini or P34 C-termini, a variant P36 that forms a thermolabile attachment to gp35, and a variant P34 with a thermolabile C-terminal attachment site.) Thermolability may be reversible, permitting reattachment of the appropriate termini when the lower temperature is restored, or it may be irreversible.

To create a variant gp37 that permits heat induced separation of the P36-P37 junction, the 5' end of gp37 DNA is randomly mutagenized using doped oligonucleotides as described above. The mutagenized DNA fragment is then recombined into T4 phage by infection of the cell containing the mutagenized DNA by a T4 phage containing two amber mutations flanking the mutagenized region. Following a low-multiplicity infection, non-amber phage are selected at low temperature on E. coli Su$^o$ at 30° C. The progeny of these plaques are resuspended in buffered and challenged by heating at 60° C. At this temperature, wild-type tail fibers remain intact and functional, whereas the thermolabile versions release the terminal P37 units and thus render those phage non-infectious.

At this stage, wild type phage are removed by: 1) adsorbing the wild type phage to sensitive bacteria and sedimenting (or filtering out) the bacteria with the adsorbed wild type phage; or 2) reacting the lysate with anti-P37 antibody, followed by immobilized Protein A and removal of adsorbed wild type phage. Either method leaves the noninfectious mutant phage particles in the supernatant fluid or filtrate, from which they can be recovered.

The non-infectious phage lacking terminal P37 moieties (and probably the rest of the tail fibers as well) are then urea treated with 6M urea, and mixed with bacterial spheroplasts to permit infection at low multiplicity whereupon they replicate at low temperature and release progeny. Alternatively, infectious phage are reconstituted by in vitro incubation of the mutant phage with wild type P37 at 30° C.; this is followed by infection of intact bacterial cells using the standard protocol. The latter method of infection specifically selects mutant phage in which the thermolability of the P36-P37 junction is reversible.

Using either method, the phage populations are subjected to multiple rounds of selection as above, after which individual phage particles are isolated by plaque purification at 30° C. Finally, the putative mutants are evaluated individually for the following characteristics: 1) loss of infectivity after incubation at high temperatures (40°–60° C.), as measured by a decrease in titer; 2) loss of P37 after incubation at high temperature, as measured by decrease in binding of P37-specific antibody to phage particles; and 3) morphological changes in the tail fibers after incubation at high temperatures, as assessed by electron microscopy.

After mutants are isolated and their phenotypes confirmed, the P37 gene is sequenced. If the mutations localize to particular regions or residues, those sequences are targeted for site-directed mutagenesis to optimize the desired characteristics.

Finally, the mutant gene 37 is cloned into expression plasmids and expressed individually in E. coli as in Example 1. The mutant P37 dimers are then purified from bacterial extracts and used in in vitro assembly reactions.

In a similar fashion, mutant gp35 polypeptides can be isolated that exhibit a thermolabile interaction with the N-terminus of P36 or the C-terminus of P34. For thermolabile interaction with P34, phage are incubated at high temperature, resulting in the loss of the entire distal half of the tail fiber (i.e. gp35-P36-P37). The only difference in the experimental protocol is that, in this case, 1) random mutagenesis is performed over the entire gp35 gene; 2) wild-type phage (and distal half-fibers from thermolabile mutants) are separated from thermolabile mutant phage that have been inactivated at high temperature (but still have proximal half tail fibers attached) by precipitating both the distal half-fibers and the phage particles containing intact tail fibers with any of the anti-distal half tail-fiber antibodies followed by Staphylococcal A-protein beads; 3) the mutant phage remaining in the supernatant are reactivated by incubation at low temperature with bacterial extracts containing wild type intact distal half fibers; and 4) stocks of thermolabile gene 35 mutants grown at 30° C. can be tested for reversible thermolability by inactivation at 60° C. and reincubation at 30° C. Inactivation is performed on a concentrated suspension of phage, and reincubation at 30° C. is performed either before or after dilution. If phage are successfully reactivated before, but not after, dilution, this indicates that their gp35 is reversibly thermolabile.

To create a gene 36 mutation with a thermolabile gp35-P36 linkage, the C-terminus of gene 36 is mutagenized as described above, and the mutant selected for reversibility. An alternative is to mutagenize gp35 to create a gene 35 mutant in which the gp35-P36 linkage will dissociate at 60° C. In this case, incubation with anti-gp35 antibodies can be used to precipitate the phage without P36-P37 and thus to separate them from the wild-type phage and distal half-tail fibers (P36-P37), since the variant gp35 will remain attached to P34.

EXAMPLE 6

Assembly of One-Dimensional Rods

A. Simple Assembly: The P37-36 chimer described in Example 2 is capable of self-assembly, but requires a P37 initiator to bind the first unit of the rod. Therefore, a P37 or a ΔP37 dimer is either attached to a solid matrix or is free in solution to serve as an initiator. If the initiator is attached to a solid matrix, a thermolabile P37 dimer is preferably used. Addition of an extract containing gp37-36, or the purified gp37-36 chimer, results in the assembly of linear multimers of increasing length. In the matrix-bound case, the final rods are released by a brief incubation at high temperature (40°–60° C., depending on the characteristics of the particular thermolabile P37 variant.)

The ratio of initiator to gp37-36 can be varied, and the size distribution of the rods is measured by any of the following methods: 1) Size exclusion chromatography; 2) Increase in the viscosity of the solution; and 3) Direct measurement by electron microscopy.

B. Staged assembly: The P37-36 variants *P37-36 and P37-36* described in Example 3 cannot self-polymerize. This allows the staged assembly of rods of defined length, according to the following protocol:

1. Attach initiator P37 (preferably thermolabile) to a matrix.

2. Add excess *gp37-36 to attach and fold as P37-36 homodimers to the N-terminus of P37.

3. Wash out unreacted *gp37-36 and flood with gp37-36*.

4. Wash out unreacted gp37-36* and flood with excess *gp37-36.

5. Repeat steps 2–4, n–1 times.

6. Release assembly from matrix by brief incubation at high temperature as above.

The linear dimensions of the protein rods in the batch will depend upon the lengths of the unit heterochimers and the number of cycles (n) of addition. This method has the advantage of insuring absolute reproducibility of rod length and a homogenous, monodisperse size distribution from one preparation to another.

EXAMPLE 7

Staged Assembly of Polygons

The following assembly strategy utilizes gp35 as an angle joint to allow the formation of polygons. For the purpose of this example, the angle formed by gp35 is assumed to be 135°. The rod unit comprises the P36-34 chimer described in Example 4, which is incapable of self-polymerization. The P36-34 homodimer is made from a bacterial clone in which both gp36-34 and gp57 are expressed. The gp57 can chaperon the homodimerization of gp36-34 to P36-34.

1. Initiator: The incomplete distal half fiber P36-37 is attached to a solid matrix by the P37 C-terminus. Thermolabile gp35 as described in Example 5 is then added to form the intact initiator.

2. Excess P36-34 chimer is added to attach a single P36-34. Following binding to the matrix via gp35, the unbound chimer is washed out.

3. Wild-type (i.e. non-thermolabile) gp35 is then added in excess. After incubation, the unbound material is washed out.

4. Steps 2 and 3 are repeated 7–8 times.

5. The assembly is released from the matrix by brief incubation at high temperature.

The released polymeric rod, 8 units long, will form a regular 8-sided polygon, whose sides comprise the P36-34 dimer and whose joints comprise the wild-type gp35 monomer. However, there will be some multimers of these 8 units bound as helices. When a unit does not close, but instead adds another to its terminus, the unit cannot close further and the helix can build in either direction. The direction of the first overlap also determines the handedness of the helix. Ten (or seven)-unit rods may form helices more frequently than polygons since their natural angles are 144° (or 128.6°). The likelihood of closure of a regular polygon depends not only on the average angle of gp35 but also on its flexibility, which can be further manipulated by genetic or environmental modification.

The type of polygon that is formed using this protocol depends upon the length of rod units and the angle formed by the angle joint. For example, alternating rod units of different sizes can be used in step 2. In addition, variant gp35 polypeptides that form angles different than the natural angle of 137° can be used, allowing the formation of different regular polygons. Furthermore, for a given polygon with an even number of sides and equal angles, the sides in either half can be of any size provided the two halves are symmetric.

What is claimed is:

1. A polypeptide comprising the gp37 tail fiber protein of bacteriophage T4 wherein internal amino acid residues of said protein have been deleted, and wherein said polypeptide has the capability to form dimers and interact with the P36 protein dimer of bacteriophage T4.

2. A polypeptide comprising a fusion protein between an amino-terminal fragment of the gp37 protein of bacteriophage T4 and a carboxy-terminal fragment of the gp36 protein of bacteriophage T4, wherein said amino-terminal fragment is recognized by an antiserum to the gp37 protein, and said carboxy-terminal fragment is recognized by an antiserum to the gp36 protein.

3. A polypeptide comprising a fusion protein between an amino-terminal fragment of the gp37 protein of bacteriophage T4 and a carboxy-terminal fragment of the gp36 protein of bacteriophage T4, wherein the polypeptide has the capability to form a dimer.

4. An isolated polypeptide homodimer comprising two gp37 polypeptides of bacteriophage T4, wherein the amino termini of said homodimer lack the capability of interacting with the carboxy termini of two gp36 polypeptides of bacteriophage T4.

5. The polypeptide of claim 1, wherein said polypeptide is lacking amino acids 99–496 of gp37.

6. The polypeptide of claim 2, wherein amino acid residues 1–242 of gp37 are fused to amino acid residues 118–221 of gp36.

7. The polypeptide of claim 6, wherein said polypeptide has the capability to form a dimer.

8. The polypeptide of claim 7, wherein the homodimer formed by said polypeptide has the capability of interacting with P37 protein dimer of bacteriophage T4.

9. The polypeptide of claim 8, wherein the dimer formed by said polypeptide has the capability of interacting with two gp36 polypeptides of bacteriophage T4.

10. The polypeptide of claim 3, wherein the homodimer formed by said polypeptide has the capability of interacting with P37 protein dimer of bacteriophage T4.

11. The polypeptide of claim 10, wherein the dimer formed by said polypeptide has the capability of interacting with two gp36 polypeptides of bacteriophage T4.

12. A polypeptide dimer comprising two modified gp37 polypeptides of bacteriophage T4, wherein the amino terminal sequences of said dimer are modified so as to be able to form a thermolabile attachment with the carboxy termini of two gp36 polypeptides of bacteriophage T4.

13. The polypeptide dimer of claim 12 wherein the thermolabile attachment is reversible.

14. The polypeptide dimer of claim 12 wherein the thermolabile attachment is irreversible.

15. A polypeptide comprising the gp37 tail fiber protein of bacteriophage T4, wherein amino acid residues have been inserted into the β-sheet of said protein, and wherein said polypeptide has the capability to form dimers and interact with the P36 protein dimer of bacteriophage T4.

16. The polypeptide of claim 1, 2, 5, 6, or 15 that consists of said protein.

17. The polypeptide of claim 1, 2, 5, 6, or 15 which is isolated.

* * * * *

UNITED STATES PATENT AND TRADEMARK OFFICE
CERTIFICATE OF CORRECTION

PATENT NO. : 5,877,279

DATED : March 2, 1999

INVENTOR(S) : Edward B. Goldberg

Page 1 of 2

It is certified that error appears in the above-identified patent and that said Letters Patent is hereby corrected as shown below:

At the title page, second column, after "OTHER PUBLICATIONS" in line 1 and before "T.E. Creighton" in line 2, please insert the following nine (9) references:

-- Steven, A.C. et al., 1988, J. Mol. Biol. 200: 351-365.

Oliver, D.B. et al., 1981, J. Mol. Biol. 153: 545-568.

Edgar, R. S. et al., 1965, Genetics 52: 1187-1200.

Ward et al., 1970, J. Mol. Biol. 54: 15-31.

Hutchison III, et al., Methods In Enzymology 202: 356-391.

Earnshaw et al., 1979, "The distal half of the tail fibre of the bacteriophage T4 rigidly linked domains and cross-β structure", J. Mol. Biol. 132: 101-131.

Freedman, 1991, "Exploiting the nanotechnology of life", Science 254(29): 1308-1310.

Levy et al., 1980, "Region-specific recombination in phage T4. II. Structure of the recombinants", Genetics 94: 531-547.

Whitesides et al., 1991, "Molecular self-assembly and nanochemistry: A chemical strategy for the synthesis of nanostructures", Science 254(29): 1312-1318. --

UNITED STATES PATENT AND TRADEMARK OFFICE
CERTIFICATE OF CORRECTION

PATENT NO. : 5,877,279
DATED : March 2, 1999
INVENTOR(S) : Edward B. Goldberg

It is certified that error appears in the above-identified patent and that said Letters Patent is hereby corrected as shown below:

At column 42, lines 59-60 (Claim 16), please delete "The polypeptide of claim 1, 2, 5, 6, or 15 that consists of said protein." and substitute therefor -- The polypeptide of claim 2, 3, 6, 10, or 11 that consists of said fusion protein. --.

Signed and Sealed this

Fourth Day of July, 2000

Attest:

Q. TODD DICKINSON

*Attesting Officer*      *Director of Patents and Trademarks*